(12) United States Patent
Chandler et al.

(10) Patent No.: US 9,715,223 B2
(45) Date of Patent: Jul. 25, 2017

(54) BIAS SETTING IN A SCENT DELIVERY SYSTEM

(71) Applicant: ScentAir Technologies, LLC, Charlotte, NC (US)

(72) Inventors: John Thurston Chandler, Charlotte, NC (US); Chad Alan Morton, Fort Mill, SC (US)

(73) Assignee: SCENTAIR TECHNOLOGIES, LLC, Charlotte, NC (US)

( * ) Notice: Subject to any disclaimer, the term of this patent is extended or adjusted under 35 U.S.C. 154(b) by 1041 days.

(21) Appl. No.: 13/939,162

(22) Filed: Jul. 10, 2013

(65) Prior Publication Data

US 2015/0019030 A1   Jan. 15, 2015

(51) Int. Cl.
  *G05D 11/00* (2006.01)
  *G05B 19/042* (2006.01)
  (Continued)

(52) U.S. Cl.
  CPC ......... *G05B 19/0426* (2013.01); *A45D 34/02* (2013.01); *A61L 9/035* (2013.01);
  (Continued)

(58) Field of Classification Search
  None
  See application file for complete search history.

(56) References Cited

U.S. PATENT DOCUMENTS 4,495,560 A * 1/1985 Sugimoto .......... B60H 1/00814
                                                137/624.11
5,175,791 A  12/1992 Muderlak et al.
(Continued)

FOREIGN PATENT DOCUMENTS

EP   2089068 B1   9/2010
GB   2413283 A   10/2005
(Continued)

OTHER PUBLICATIONS

International Search Report and Written Opinion in International Application No. PCT/US14/45977, mailed on Oct. 15, 2014, 7 pages.

(Continued)

*Primary Examiner* — Jason Mitchell

(74) *Attorney, Agent, or Firm* — Kilpatrick Townsend & Stockton LLP

(57) ABSTRACT

A scent delivery system includes scent delivery units that are configured to deliver scent at a variable scent level by being turned on and off successively according to a variable duty cycle. The scent delivery units are associated with corresponding base scent settings. The scent delivery system also includes a central controller configured to control the scent delivery units by generating command data based on a scenting schedule that indicates a desired activation time for more than one implicated scent delivery unit. The scenting schedule is configured to further indicate a scent level bias to be applied to the base scent settings that are associated with different of the implicated scent delivery units. The central controller is configured to generate the command data, based upon a variation in the scent level bias, that takes into account a corresponding variation to duty cycles that are associated with different of the implicated scent delivery units and to communicate the command data to the different implicated scent delivery units.

28 Claims, 11 Drawing Sheets

(51) Int. Cl.
*G05D 7/06* (2006.01)
*A61L 9/03* (2006.01)
*A61L 9/12* (2006.01)
*A61L 9/14* (2006.01)
*A45D 34/02* (2006.01)
*B05B 12/02* (2006.01)
*G06Q 10/06* (2012.01)
*H04L 29/08* (2006.01)
*A61M 21/00* (2006.01)

(52) U.S. Cl.
CPC ............... *A61L 9/125* (2013.01); *A61L 9/14* (2013.01); *B05B 12/02* (2013.01); *G05D 7/0629* (2013.01); *G06Q 10/0631* (2013.01); *G06Q 10/06314* (2013.01); *H04L 67/125* (2013.01); *A61L 2209/11* (2013.01); *A61L 2209/111* (2013.01); *A61L 2209/132* (2013.01); *A61L 2209/16* (2013.01); *A61M 2021/0016* (2013.01); *A61M 2205/3561* (2013.01); *A61M 2205/3584* (2013.01); *A61M 2205/3592* (2013.01); *A61M 2205/502* (2013.01); *G05B 2219/25419* (2013.01)

(56) References Cited

U.S. PATENT DOCUMENTS

| | | |
|---|---|---|
| 5,795,147 A | 8/1998 | Saxena et al. |
| 5,949,522 A * | 9/1999 | Manne .................. A61L 9/122 261/104 |
| 5,986,439 A * | 11/1999 | Pletta .................... H02J 7/1438 322/18 |
| 6,039,212 A | 3/2000 | Singh |
| 6,379,242 B1 * | 4/2002 | Wiseman, Sr. ......... A61L 9/14 222/647 |
| 6,443,434 B1 | 9/2002 | Prather |
| 6,581,915 B2 | 6/2003 | Bartsch et al. |
| 6,681,110 B1 | 1/2004 | Crookham et al. |
| 6,834,847 B2 | 12/2004 | Bartsch et al. |
| 6,994,328 B2 | 2/2006 | Watkins et al. |
| 7,066,218 B1 | 6/2006 | Fleming et al. |
| 7,160,515 B2 | 1/2007 | Murdell et al. |
| 7,223,361 B2 | 5/2007 | Kvietok et al. |
| 7,503,668 B2 | 3/2009 | Porchia et al. |
| 7,540,433 B2 | 6/2009 | Fleming et al. |
| 7,665,673 B2 | 2/2010 | Hagleitner |
| 7,691,336 B2 | 4/2010 | Westring |
| 7,778,635 B2 | 8/2010 | Crookham et al. |
| 7,832,655 B2 | 11/2010 | Tollens et al. |
| 7,913,933 B2 | 3/2011 | Van Roemburg |
| 7,932,482 B2 | 4/2011 | Norwood et al. |
| 7,981,367 B2 | 7/2011 | Kvietok et al. |
| 8,016,207 B2 | 9/2011 | Kvietok et al. |
| 8,061,628 B1 | 11/2011 | Kvietok et al. |
| 8,119,064 B2 | 2/2012 | Woo et al. |
| 8,210,448 B2 | 7/2012 | Kvietok et al. |
| 8,349,251 B2 | 1/2013 | Woo et al. |
| 8,372,349 B1 * | 2/2013 | Shotey ................ A61L 9/122 134/104.1 |
| 2003/0020185 A1 * | 1/2003 | Cox .................... A01M 1/2033 261/26 |
| 2006/0175426 A1 * | 8/2006 | Schramm ............ A01M 1/2033 239/69 |
| 2006/0261179 A1 | 11/2006 | Davies et al. |
| 2007/0258849 A1 | 11/2007 | Kent |
| 2008/0233001 A1 * | 9/2008 | Ricciardi ................. A61L 2/22 422/20 |
| 2009/0001179 A1 * | 1/2009 | Dempsey ............. F24F 11/0001 236/49.3 |
| 2009/0117261 A1 * | 5/2009 | Sakai .................. B41J 2/04541 427/66 |
| 2009/0125641 A1 | 5/2009 | Garbow et al. |
| 2009/0169420 A1 | 7/2009 | Pollizi et al. |
| 2009/0184432 A1 * | 7/2009 | Cittadino ............... A61L 9/122 261/26 |
| 2009/0312876 A1 * | 12/2009 | Yoneda ................ G01F 1/6965 700/282 |
| 2010/0042262 A1 * | 2/2010 | Niezgoda ........... B01D 46/0038 700/282 |
| 2010/0078497 A1 * | 4/2010 | Gasper ..................... A61L 9/02 239/6 |
| 2010/0155414 A1 | 6/2010 | Hu |
| 2010/0179701 A1 | 7/2010 | Gilbert et al. |
| 2011/0089260 A1 | 4/2011 | Van Roemburg |
| 2011/0111700 A1 | 5/2011 | Hackett |
| 2011/0270448 A1 | 11/2011 | Kantor et al. |
| 2011/0295400 A1 | 12/2011 | Samain |
| 2011/0295434 A1 | 12/2011 | Luc et al. |
| 2013/0081541 A1 | 4/2013 | Hasenoehrl et al. |
| 2014/0067130 A1 * | 3/2014 | Pillai .................. H04L 12/2816 700/275 |
| 2015/0009848 A1 * | 1/2015 | Miki ................. H04W 72/1231 370/252 |
| 2015/0019029 A1 | 1/2015 | Chandler et al. |
| 2015/0019041 A1 | 1/2015 | Chandler et al. |
| 2015/0076716 A1 | 3/2015 | Roemburg et al. |

FOREIGN PATENT DOCUMENTS

| | | |
|---|---|---|
| WO | WO0209776 A2 | 2/2002 |
| WO | WO2007056147 A1 | 5/2007 |
| WO | WO2008025168 A1 | 3/2008 |
| WO | WO2008144202 A2 | 11/2008 |
| WO | WO2009059373 A1 | 5/2009 |
| WO | WO2009127069 A1 | 10/2009 |

OTHER PUBLICATIONS

International Search Report and Written Opinion in International Application No. PCT/US14/45971, mailed on Oct. 15, 2014, 8 pages.
Notice of Allowance Office Action mailed May 20, 2016, issued in U.S. Appl. No. 13/939,159, 21 pages.
Notice of Allowance Office Action mailed Jun. 2, 2016, issued in U.S. Appl. No. 13/939,165, 18 pages.
Non-Final Office Action dated Jan. 21, 2016, issued in U.S. Appl. No. 13/939,159, 22 pages.
Non-Final Office Action dated Jan. 21, 2016, issued in U.S. Appl. No. 13/939,165, 20 pages.
Iallergy, Oskar Evaporator Humidifier Black w/Bonus Silver Cube [online], [retrieved on Apr. 21, 2013]. Retrieved from the Internet: www.iallergy.com/product1103/product_info.html, 2 pages.

* cited by examiner

400

```
SCHEDULED EVENT                                    _  x
  Schedule Name:  [Schedule 1            ]  (404)
     Event Type:  Calendar ☐   Weekly ☒  (406)
   Group or Unit: Group ☐      Unit ☒    (408)
    Description:  [Machine_A            ▼]  (410)
          Days:  Mon☐ Tue☐ Wed☒ Thu☐ Fri☐ Sat☐ Sun☐ (412)
        On Time: [ 9:30 ]  (414)
       Off Time: [14:30 ]  (416)
    Bias Setting:[  0   ]  (418)
    Anti-Event?: YES☐ NO☒  (420)            SAVE
```

402

```
SCHEDULED EVENT                                    _  x
  Schedule Name:  [Schedule 2            ]  (424)
     Event Type:  Calendar ☐   Weekly ☒  (426)
   Group or Unit: Group ☐      Unit ☒    (428)
    Description:  [Machine A            ▼]  (430)
          Days:  Mon☐ Tue☐ Wed☒ Thu☐ Fri☐ Sat☐ Sun☐ (432)
        On Time: [15:00 ]  (434)
       Off Time: [21:00 ]  (436)
    Bias Setting:[ +15  ]  (438)
    Anti-Event?: YES☐ NO☒  (440)            SAVE
```

```
SCHEDULED EVENT                                    _  x
  Schedule Name:  [Schedule 1              ]  (804)
     Event Type:  Calendar ☐    Weekly ☒   (806)
  Group or Unit:  Group ☒       Unit ☐     (808)
    Description:  [Group1                ▼]  (810)
          Days:  Mon☐ Tue☐ Wed☒ Thu☐ Fri☐ Sat☐ Sun☐  (812)
       On Time:  [ 9:30 ]  (814)
      Off Time:  [14:30 ]  (816)
   Bias Setting: [  0   ]  (818)
    Anti-Event?: YES☐ NO☒  (820)              [SAVE]
```

802

```
SCHEDULED EVENT                                    _  x
  Schedule Name:  [Schedule 2              ]  (824)
     Event Type:  Calendar ☐    Weekly ☒   (826)
  Group or Unit:  Group ☒       Unit ☐     (828)
    Description:  [Group1                ▼]  (830)
          Days:  Mon☐ Tue☐ Wed☒ Thu☐ Fri☐ Sat☐ Sun☐  (832)
       On Time:  [15:00 ]  (834)
      Off Time:  [21:00 ]  (836)
   Bias Setting: [ +15  ]  (838)
    Anti-Event?: YES☐ NO☒  (840)              [SAVE]
```

FIG. 8

BIAS SETTING IN A SCENT DELIVERY SYSTEM

CROSS-REFERENCE TO RELATED APPLICATION

This application is related to U.S. patent application Ser. No. 13/939,165, filed Jul. 10, 2013, titled "SCENT DELIVERY SYSTEM SCHEDULING" and U.S. patent application Ser. No. 13/939,159, filed Jul. 10, 2013, titled "RELATEDNESS IN A SCENT DELIVERY SYSTEM," which are hereby incorporated by reference in their entirety.

TECHNICAL FIELD

This document describes a scent delivery system that enables scent levels of one or more scent delivery machines to be varied.

BACKGROUND

Products can be developed to deliver scents or aromas in commercial or office environments, such as in a hotel or a retail setting. The scents can improve a customer's perception of the environment and can help influence customer behavior. Scents and systems can be customized to reflect and complement various activities, events, brands, moods, or environments.

SUMMARY

In one general aspect, a scent delivery system includes scent delivery units that are configured to deliver scent at a variable scent level by being turned on and off successively according to a variable duty cycle. The scent delivery units are associated with corresponding base scent settings. The scent delivery system also includes a central controller configured to control the scent delivery units by generating command data based on a scenting schedule that indicates a desired activation time for more than one implicated scent delivery unit. The scenting schedule is configured to further indicate a scent level bias to be applied to the base scent settings that are associated with different of the implicated scent delivery units. The central controller is configured to generate the command data, based upon a variation in the scent level bias, that takes into account a corresponding variation to duty cycles that are associated with different of the implicated scent delivery units and to communicate the command data to the different implicated scent delivery units.

Implementations may include one or more of the following features. For example the central controller may be configured to vary the duty cycles that are associated with different of the implicated scent delivery units based on the scent level bias by varying the duty cycles according to an arithmetic function. The central controller may be configured to vary the duty cycles that are associated with different of the implicated scent delivery units based on the scent level bias by varying the duty cycles according to an geometric function. The central controller may be configured to vary the duty cycles that are associated with different of the implicated scent delivery units based on the scent level bias and scent types that are associated with different of the implicated scent delivery units. The central controller may be configured to vary cycle times that are associated with different of the implicated scent delivery units based on the scent level bias. The scent delivery units may be configured to turn on and off successively according to a variable duty cycle that ranges between 5% and 95%. The central controller may be configured to vary the base scent settings that are associated with different of the implicated scent delivery units based on scent types that are associated with different of the implicated scent delivery units. The scent delivery units may be configured to deliver scent at a variable scent level by varying one or more of fan speed, nozzle pressure, and compressor power of each scent delivery unit. Based upon a variation in the scent level bias, the central controller may send command data that takes into account a corresponding variation to a corresponding one or more of fan speed, nozzle pressure, and compressor power of the implicated scent delivery units. The central controller may generate and send a signal to multiple scent delivery units, where the signal reflects a duty cycle that reflects power characteristics to be applied in successively turning the scent delivery units on and off. The central controller may generate and send a signal to multiple scent delivery units, where the signal is a pulse that corresponds to the multiple scent delivery units being turned on or off. The central controller may generate and send a different signal to each of at least two scent delivery units, where each different signal reflects a duty cycle that reflects power characteristics to be applied in successively turning a corresponding scent delivery unit on and off. The central controller may generate and send signals to each of at least two scent delivery units, where the signals sent to a first of the at least two scent delivery units vary in time relative to the signals sent to a second of the at least two scent delivery units. The signals may include pulses that correspond to the corresponding scent delivery unit being turned on or off.

Other embodiments of this aspect include corresponding methods and computer-readable storage mediums.

The details of one or more implementations described in this specification are set forth in the accompanying drawings and the description below. Other potential features and aspects of the subject matter will become apparent from the description, the drawings, and the claims.

DESCRIPTION OF DRAWINGS

FIG. 4 shows sample graphical windows illustrating inputting information regarding a scheduled event for one scent delivery unit.

FIG. 8 shows sample graphical windows illustrating inputting information regarding a scheduled event for a group of scent delivery units.

Like reference symbols in the various drawings indicate like elements.

DETAILED DESCRIPTION

A scent delivery system can include one or more scent delivery units that are configured to release a fragrance or a scent in a controlled manner. By distributing the one or more scent delivery units, or machines, throughout a scenting environment, a desired scent profile can be generated in the environment. In some scenting environments, such as a hotel, the desired scent profile can vary according to location within the space, time of day, day of the week, etc. By incorporating a network controlled scent delivery system, a user can control the one or more scent delivery units, either individually or as a group, through a central controller. As further detailed below, one or more scent intensities associated with a single unit or a group of units may be scheduled and adjusted through the central controller. In some cases, a single adjustment may be made to effect a change in a bias setting applicable to scent intensities of multiple scent delivery units.

Figure 1:
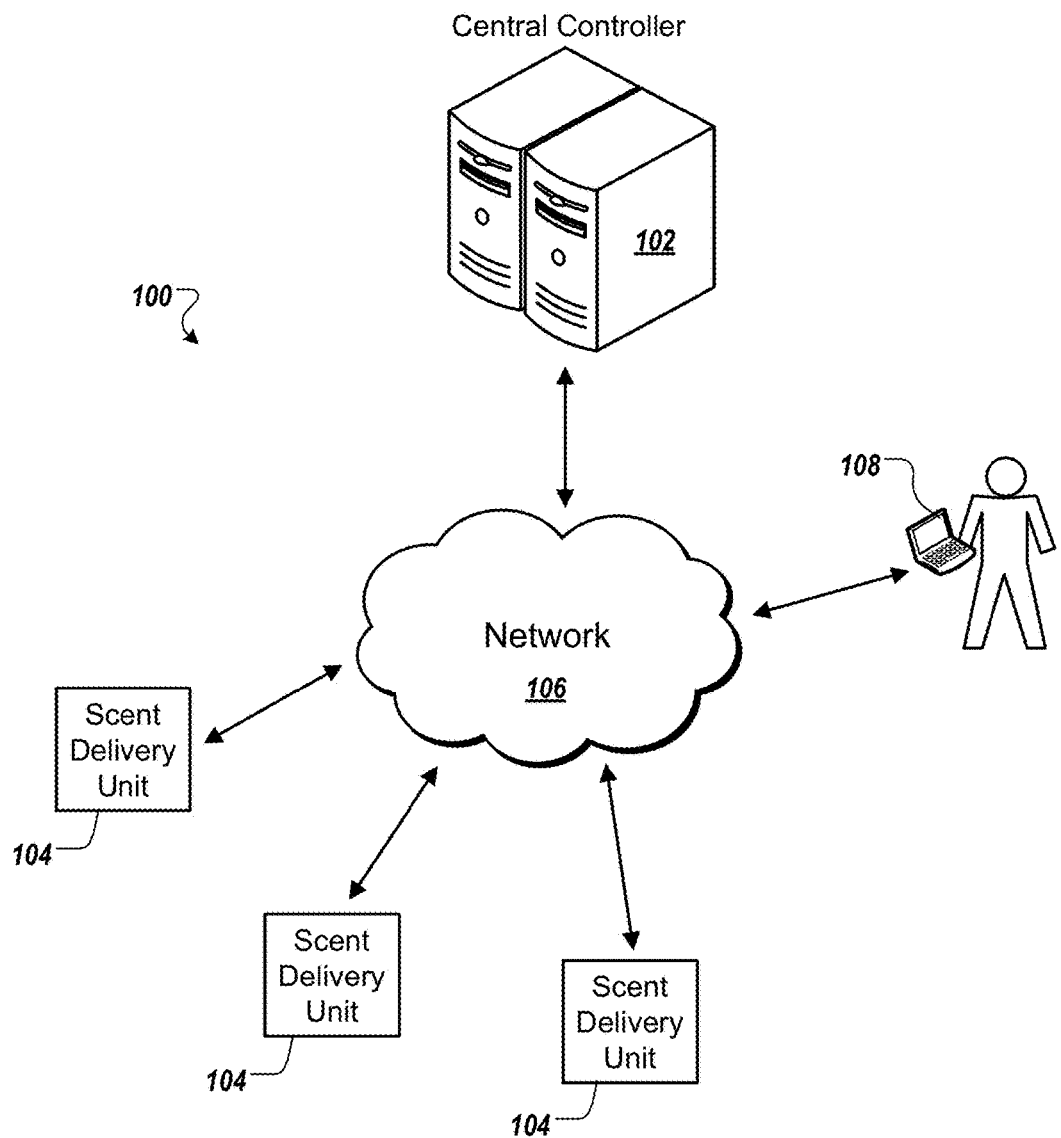
FIG. 1 is a block diagram of a scent delivery system.

Referring to FIG. 1, a scent delivery system 100 includes a central controller 102 that is connected to one or more scent delivery units 104 across a network 106. The central controller 102 is configured to control the activation and deactivation of each scent delivery unit 104 based on a user-defined schedule. The central controller 102 can also include, or have access to, a database that contains information about each scent delivery unit 104. Such information may include, for example, the location and scent type of each scent delivery unit 104.

The network 106 is configured to enable direct or indirect communications between the central controller 102, the scent delivery units 104, and a user device 108. Examples of the network 106 include the Internet, Wide Area Networks (WANs), Local Area Networks (LANs), analog or digital wired and wireless telephone networks (e.g., Public Switched Telephone Network (PSTN), Integrated Services Digital Network (ISDN), and Digital Subscriber Line (xDSL)), radio, television, cable, satellite, and/or any other delivery or tunneling mechanism for carrying data. In some implementations, the network 106 includes wired or wireless network systems including, but not limited to, wired Ethernet, Wi-Fi, and ZigBee. In some implementations, the network 106 may be made up of direct connections, either wired or wireless, between the scent delivery units 104 and the central controller 102.

Each scent delivery unit 104 is configured to deliver one or more scents and includes a mechanism for releasing the one or more scents into the air. Each scent delivery unit 104 can also include a network module for communicating with the central controller 102 through the network 106. In some implementations, one or more scent delivery units 104 can be associated with a separate network module to establish communication with the central controller 102. This way, for example, pre-existing scenting machines without networking capabilities may be deployed in the system 100 and controlled via the central controller 102. In some implementations, the scent delivery units 104 can directly communicate with each other, for example via a mesh network, so that establishing communication between each scent delivery unit 104 and the central controller 102 may not be required.

In one implementation, each scent delivery unit 104 includes a scent reservoir and an atomizing device in fluid communication with the scent reservoir. In one example, the scent reservoir is a cartridge bottle containing scented liquid, for example a fragrant oil mixture, that emits a desired scent for the particular scent delivery unit 104. The atomizing device can be, for example, a venturi-type atomizer that uses a high velocity airstream, generated by an integrated or a separate compressor, to draw in and atomize the liquid in the cartridge bottle into small particles (e.g., under 10 microns in diameter) that can be dispersed into the air to generate the desired scent. Movement of atomized scent particles within a scenting environment can further be aided by airflow generated by a heating, ventilation, and air conditioning (HVAC) system.

A level of scent (also referred to as an intensity of scent) associated with each scent delivery unit 104 may need to be adjusted depending on the particular application and may be done so in one of several ways. For example, the pressure and/or velocity of the atomizing air stream can be increased to atomize and disperse more scent particles into the air, thus resulting in an increased scent level. Alternatively, or additionally, precise control of scent levels may be achieved by operating the scent delivery unit 104 under a duty cycle. That is, by turning the scent delivery unit 104 on and off successively in accordance with power characteristics indicated by the duty cycle during the time of activation, the total amount of scent particles released into the environment, and therefore the scent level, can be precisely controlled. A cycle time of each scenting unit 104, i.e. the period of time during which one on-off cycle occurs, may also be varied to achieve a desired result. For example, given the same duty cycle, a scenting unit 104 operating under a long cycle time will result in a longer off time between each cycle, thereby increasing the period during which a customer may regain his/her olfactory sensitivity and helping to reduce odor fatigue that may result from prolonged exposure to scent.

As used herein, "scent level" may refer to a total number of scent particles released in an environment during a given amount of time. Under this definition, a scenting scheme, for example, that constantly releases N number of particles into the environment per second during activation time T may be said to produce the same scent level as an alternative scenting scheme in which 2×N number of particles per second are released during time T under a duty cycle of 50%—since in both cases, the same total number of scent particles would be released during time T. Under the latter scenting scheme, if the particles are released at a constant rate during the ON portion of the duty cycle, then increasing or decreasing the duty cycle would result in a corresponding change to the scent level.

Notably, a strength of the scent as perceived by the user may be related but not directly linked to the scent level. For example, even if the same machine operates under different scent levels during multiple periods of activation, the strength of the scent as perceived by the user across such periods may not change. This is because a multitude of other factors, such as temperature, humidity, type of scent, number of people in the room, HVAC settings, etc., not to mention an individual's scent perception abilities, may affect how strong a particular scent is perceived by the user within the particular scenting environment.

In some implementations, each scent delivery unit 104 may be associated with a base scent setting. The base scent setting may refer to machine-specific parameter settings that enable the machine to create a desired scent effect at a particular location (e.g., a room of a building). Determining the parameter settings to create a desired scent effect requires consideration of, for example, the machine's environment at the scent location (e.g., how close is the machine to a window, a vent, or a door), the scent type, etc. The base scent setting may, for example, refer to an optimal cycle time (e.g., 120 seconds) and/or duty cycle (e.g., 50%) for the particular machine that achieves the desired scent effect at the scent location. In some cases, the base scent setting may additionally or alternatively refer to other variable parameters of the machine, such as fan speed, nozzle pressure, compressor power, etc., that ultimately have an impact on the scent level.

In some implementations, the base scent setting is determined at the time of installation of the machine at the scent location. In other implementations, the base scent setting may be determined prior to or subsequent to installation. The determined base scent setting may be set by a user at the machine through user interactions with the machine itself (in implementations in which scent setting controls are included in the machine) and/or may be set by a user through interactions with a user device 108. The base scent setting may be set at the time of installation as part of the installation process and/or may be set subsequent to installation of the machine as part of a later machine initialization process. After being set, the base scent setting may be subsequently changed by a user at the machine through interactions with the machine itself and/or by a user (local or remote to the machine) through interactions with the user device 108. In some cases, the central controller and/or the machine may require additional user credentials for changing the base scent setting. For example, only a user with systems administrator privileges may be able to change the base scent setting.

The central controller 102, which can be, for example, a rack mountable server, is configured to maintain a database that includes information about each scent delivery unit 104 in the system 100. This information can include, for example, the physical as well as network location of each scent delivery unit 104 along with information about the type of scent it contains. The database can also include, for example, information about a base scent setting of each scenting unit 104, as specified by, for example, its cycle time and duty cycle. In some implementations, information about the base scent setting of each scent unit 104, or any other machine-specific parameter, may be directly stored in or otherwise accessed by each scent unit 104. Under this implementation, each scent unit 104 may send or otherwise make accessible the machine-specific parameters to the central controller 102 upon request.

The central controller 102 may also be configured to maintain a master schedule that can be accessed by the user and that incorporates multiple scheduled events for each scent delivery unit 104. Each scheduled event specifies control logic to activate and deactivate the one or more scent delivery units 104 during desired one or more time periods. The control logic may activate and deactivate the one or more scent delivery units 104 individually and/or in user-defined groups. In one implementation, the master schedule may refer to an aggregate of all scheduled events for all scent delivery units within the network controlled system 100. The master schedule may be stored in or otherwise accessible through the central controller 102. In some cases, the master schedule may refer to a group of particular scheduled events, for example, all scheduled events pertaining to scent delivery units positioned in a certain location (e.g., a particular building, a particular floor of a building, or a particular room or set of rooms in a building). In some cases, the master schedule may include a collection of other master schedules.

To program a desired scenting schedule for the one or more scent delivery units 104, a user can access the central controller 102 through use of the user device 108. The user device 108 may be, for example a personal computer or a mobile device. In some implementations, the user device 108 is configured to communicate with the central controller 102 through the network 106. In some implementations, the user device 108 may additionally or alternatively access the central controller 102 by directly connecting to it without going through a network. Notably, while only one user device 108 is shown in FIG. 1, it should be understood that the system 100 can include multiple user devices 108, each of which enables a different user to communicate with the central controller 102 to, for example, schedule one or more scenting events. The one or more scenting events are compiled by the central controller 102 into a master schedule, which, in some implementations, may be presented in whole or in part to the user of the user device 108 to facilitate event scheduling.

The central controller 102 can include a user interface component that allows the user to make changes to the master schedule and to access and update the database that includes information about each scent delivery unit 104. In some implementations, the user interface component is a user interface web component that allows the user to make changes to the master schedule and to access and update the scent delivery unit database over the World Wide Web.

Based on the master schedule and the machine-specific information available from the database, the central controller 102 can generate a set of machine-specific command data that corresponds to the desired schedule. In one implementation, the central controller 102 generates, for each scent delivery unit 104, command data that is made up of a series of on and off commands, where the frequency and duration of the on and off periods are based on the specified cycle time and duty cycle of each scenting unit, and transmits this data in real-time to the corresponding scent delivery units. In response to this command data, each scent delivery unit 104 may simply turn on (i.e., deliver scent) in real-time in response to and upon receiving a "turn ON" command and turns off (i.e., not deliver scent) in real-time in response to and upon receiving a "turn OFF" command. Alternatively, the central controller 102 may generate, for each scent delivery unit 104, a single turn ON command that corresponds to a scheduled activation and a single turn OFF command that corresponds to a scheduled deactivation. Under this type of control scheme, the scent delivery unit 104 may be configured to constantly deliver scent during the period of activation, instead of being turned on and off successively according to a duty cycle.

In other implementations, the central controller 102 can generate and transmit command data that contains all required information for each scent delivery unit 104 to perform as scheduled (e.g., transmits command data directing the unit to activate from 1:30 pm to 3:30 pm on Wednesday, July 7th using a scent cycle time of 300 seconds and a 50% scent duty cycle). Each scent delivery unit 104 can receive and independently act on a command to activate during a certain time period at a specified scent level. Notably, in these implementations, the scent delivery units 104 may have additional processing and memory capabilities that enable them to process the more complex command data received from the central controller 102. Also, the scent delivery unit 104 may be configured to synchronize its activation and deactivation schedules with those of the other scent delivery units 104.

Because each scent unit 104 may be associated with an optimal base scent setting (e.g., cycle time and duty cycle), the user may schedule the desired activation time of a unit, for example by creating a scheduled event, without having to specify any of the parameters of the base scent setting (e.g., cycle time and/or the duty cycle) for the scheduled event. In this case, the central controller 102 may simply generate command data to reflect the desired activation time and the base scent setting associated with the unit. In other cases, the generated command data may not include any information about the base scent setting parameters (e.g., cycle time and/or the duty cycle), with the unit itself being configured to simply operate during the desired activation time according to its optimal base scent setting.

In other implementations, the user may wish to create a scheduled event that deviates from the base scent setting for a machine. For example, the user may walk through the lobby during a particular scheduled activation time and feel that the scent provided by a particular machine is too weak (i.e., should be perceived as being stronger). In this case, the user may access the central controller 102 and update the base scent setting for the responsible machine to, for example, have a higher scent level (e.g., by increasing the duty cycle). This, however, may impact other scheduled scenting events that use the same machine, which may be undesirable. Alternatively, the user may access the central controller 102 and update just the particular scheduled event during which the stronger scent is desired. Notably, unlike sound, light, temperature, etc., which have a desired setpoint that can be easily quantified (e.g., decibel, lumen, degree Celsius, etc.), the desired perception of scent may be harder to define. Accordingly, instead of setting an absolute scent setpoint, the user may, for example, associate the particular scheduled event with a positive or negative scent level bias to increase or decrease, respectively, the associated duty cycle relative to the base scent setting. Other scheduled events that control the same machine without indicating this bias will continue to operate according to the base scent setting associated with the machine. The scheduled events may indicate the bias either directly or indirectly.

As noted above, the base scent setting of each machine (e.g. cycle time and duty cycle) may be set at the time of installation and may be optimized in view of the machine's location, scent type, etc. For example, the manufacturer, at the time of installation, may carefully analyze the particular scenting environment—through trial and error, internally developed metrics, instrumented analysis, or use of a professional perfumer, just to name a few methods—to come up with the ideal base scent setting for a particular machine. However, during normal usage, a user may want to deviate from the base scent setting depending on, for example, dynamic variables specific to a given scent event (e.g., number of people in the room during the event, HVAC settings during the event, etc.). Such dynamic variables may not have been present or otherwise considered during the time of installation. As such, the user may schedule a desired scent event in consideration of such dynamic variables by simply determining the appropriate bias value relative to the base scent level—without altering the base scent level itself.

In other implementations, the user may wish to change, for example, the scent levels (e.g., by changing the duty cycle) of multiple machines, where each machine may be configured, via the base scent setting, to operate at different cycle times and/or duty cycles. In this implementation, as detailed further below, the user may indicate a single scent level bias that will correspondingly alter the scent levels (e.g., duty cycles) of the multiple machines while preserving their base scent settings. In most cases, a duty cycle of the machines may be variable in the range between around 5% to around 95%.

Figure 2:
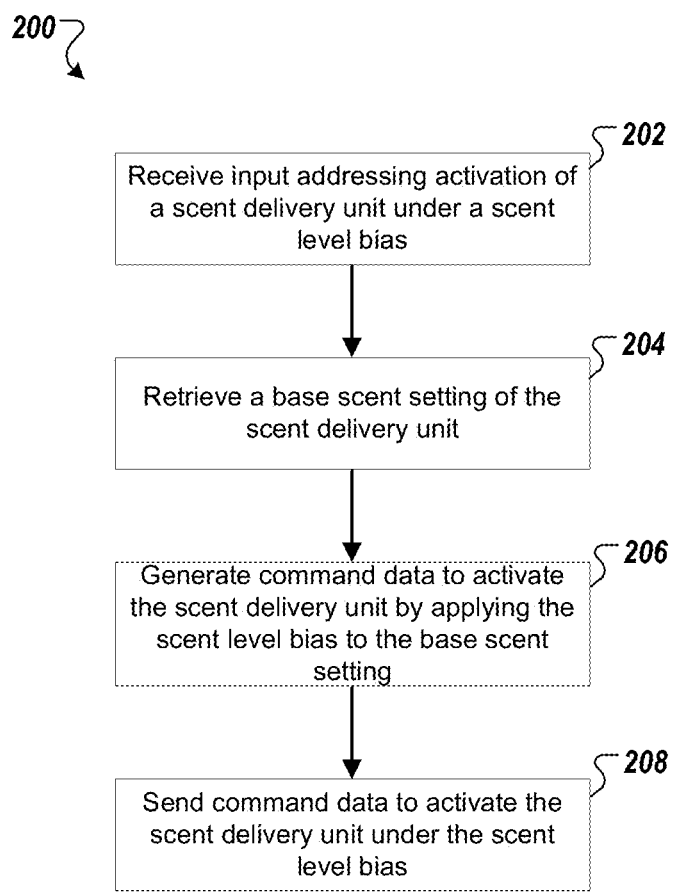
FIG. 2 is a flow chart of a process for activating a scent delivery unit within the scent delivery system.

FIG. 2 is a flowchart of an example process 200 in which a system may alter a scent level of a scent delivery unit during a particular activation period without permanently altering the associated base scent setting. Briefly, the process 200 includes receiving input addressing the activation of a scent delivery unit along with an associated scent level bias (202), and retrieving the base scent setting associated with said scent delivery unit (204). Based on the received input and the retrieved base scent setting, the system generates command data to activate the scent delivery unit by applying the received scent level bias to the retrieved base scent setting (206). The generated command data is then sent to the scent delivery unit (208).

Here, generating command data may include generating a set of machine-specific instructions that incorporates all scheduled events for a given machine and instructs said machine when to turn on and off. In some implementations, the generated command data may be stored in a machine-specific table of instructions that does not lead to conflicting machine behavior. In some implementations, generating command data may include updating and/or revising the master schedule of events to eliminate instances of conflicting machine behavior.

Sending command data may include transmitting the generated command data to the one or more scent delivery units across a network (e.g., network 106). In some implementations, the command data may be sent in real-time as they are generated. Alternatively, or additionally, the command data may be sent at predetermined time intervals, e.g., once every minute. In some cases, the command data may be sent in response to and upon receiving instructions from the user. In other cases, the command data may be sent in response to and upon receiving a query for instructions, e.g., from the scent delivery unit.

In one implementation example, the process 200 of FIG. 2 may be implemented by the system 100 of FIG. 1. In this implementation, the central controller 102 may receive input addressing the activation of a scent delivery unit under a scent level bias (202) when the user schedules a scenting event that includes the scent delivery unit and further indicates that a bias should be applied for the particular event. For example, a user-entered scheduled event may indicate that the first scent delivery unit should be activated every Monday from 9:00 am to 5:00 pm under a +15 bias. Particular values that may be associated with the bias will be discussed further below; however, the positive value in this example indicates that the user desires a higher scent level during the indicated activation period. The higher desired scent level may indicate that the user wants to perceive a stronger scent during the noted activation period compared to other activation periods for the same machine. Alternatively, or additionally, the higher desired scent level may indicate that the user wants to perceive the same strength of the scent during the noted activation period as in other activation periods for the same machine, but that particular conditions of the scenting environment during the noted activation period require a higher scent level to achieve the same perceived effect. For example, there may be higher foot traffic during the noted activation period. In some cases, the user-entered scheduled event may indicate that a group of scent delivery units should be activated as scheduled. Either way, before the scent delivery unit can be activated according to the user input, the central controller 102 will need to determine what command data should be sent to the scent delivery unit.

In operation 204, the central controller 102 retrieves the base scent setting of the scent delivery unit from operation 202. Because the scent level bias information received in operation 202 indicates a relative increase/decrease as opposed to an absolute setpoint, the central controller 102 may need to know the base scent setting in order to generate the appropriate command data. In some implementations, the central controller 102 may include or otherwise have access to a database that stores the information pertaining to each scent delivery unit, including its base scent setting. In some cases, the central controller 102 may obtain such information directly from the individual scent delivery units. In some cases, each scheduled event may be pre-loaded with the base scent setting information for each machine included in the scheduled event, and this information may be passed onto the central controller 102 along with the received input addressing the machine's activation.

The central controller 102 will proceed to generate, in operation 206, command data to activate the scent delivery unit in a manner that accounts for the scent level bias. For example, if the central controller 102 receives input, in operation 202, from a newly entered scheduled event indicating that a particular scent delivery unit should be activated daily from 1:00 pm to 6:00 pm under a scent level bias of +15, and if the central controller 102 knows, from operation 204, that this particular scent delivery unit is associated with a base scent setting having a cycle time of 300 seconds and a duty cycle of 50%, then the central controller 102 will generate command data that applies the +15 bias to the duty cycle of 50%. In this example, the central controller 102 may simply add 15 percentage points to the base duty cycle of 50%. Accordingly, the command data will indicate that the noted scent delivery unit should activate daily from 1:00 pm to 6:00 pm, and that during this activation period, the scent delivery unit should turn on and off successively for periods of 195 seconds and 105 seconds, respectively.

In some implementations, the central controller 102 may use an arithmetic function in applying the scent level bias to the base scent level. For example, a +15 bias may simply be added to a base duty cycle of 50%, thereby yielding a revised duty cycle of 65% (i.e., 50+15) for the generated command data. Alternatively, or additionally, the central controller 102 may use a geometric function in applying the scent level bias to the base scent level. For example, a +15 bias may indicate a percentage increase to the base duty cycle of 50%, thereby yielding a revised duty cycle of 57.5% (i.e., 50×1.15) for the generated command data.

In some implementations, the scent level bias, as inputted by the user, may be applied in a different manner by the central controller 102 depending on a machine-specific parameter and a pre-defined algorithm related to said parameter. In one implementation, prior to being applied to the base scent level, the scent level bias may be scaled up or down by a known amount in accordance with an algorithm. For example, a machine having one type of a scent may have the full bias applied to its base scent level, while a different machine having a different type of a scent may have only half of the bias applied to its base scent level. In some cases, the scaling factor for the scent level bias may vary depending on the base scent level. For example, the scaling factor may be inversely proportional to the base scent level. In other implementations, the scaling factor for the scent level bias may vary according to a known calibration curve for each machine and/or scent type.

As noted above, the duty cycle may be varied between around 5% to around 95%. In some cases, each scent delivery unit may be associated with its own range of duty cycle. In either case, if applying a scent level bias to the base scent level of a particular machine would result in that machine's duty cycle going beyond the specified range, the central controller 102 may instead generate, for that particular machine, command data that corresponds to the maximum or minimum specified duty cycle. In some cases, when a scheduled event controls activation of multiple machines under a single scent level bias, the central controller 102 may generate command data for all machines based on a reduced scent level bias that would not push any of the machines beyond the specified range of duty cycle.

Figure 3:
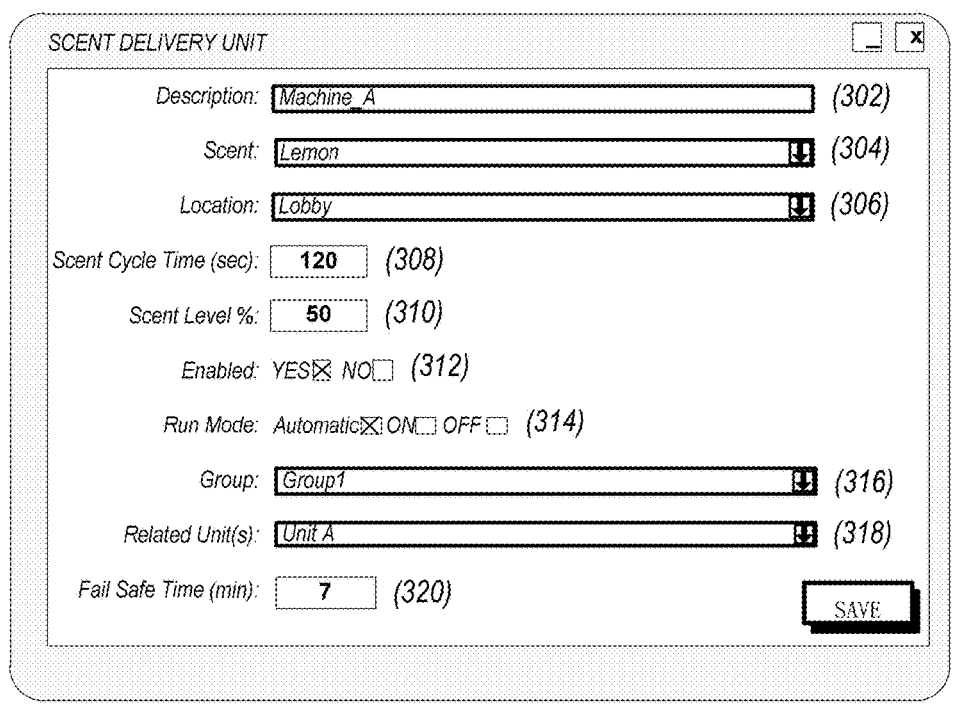
FIG. 3 shows sample graphical windows illustrating inputting information regarding a scent delivery unit.

FIGS. 3 and 4 illustrate a series of exemplary graphical user interface (GUI) windows 300, 400, and 402 associated with the scent delivery system 100. The graphical windows 300, 400, and 402 may be provided by the user interface component of the central controller 102 and may be accessed by one or more users over, for example, the World Wide Web using a browser application resident on one or more of the user devices 108.

Referring to FIG. 3, the graphical window 300 illustrates how data pertaining to a particular scent delivery unit may be entered. The data may be maintained in a database contained within or otherwise accessible to the central controller 102 and may be accessed and/or updated by one or more users, for example, through use of one or more of the user devices 108 across the network 106. The particular types and styles of GUI input elements, i.e., entry boxes, check boxes, pull-down menus, etc., as depicted in the exemplary windows are for illustrative purposes only and may be altered as necessary depending on system requirements, user preferences, scenting environment, etc.

The graphical window 300 illustrates data entry pertaining to a scent delivery unit named "Machine_A," as indicated in entry box 302. In the same window 300 or in another interface, the name Machine_A may further be associated with a network address or the like such that the central controller 102 may send command data thereto in order to control Machine_A as dictated by the master schedule.

In pull-down box 304, the scent type associated with Machine_A may be identified. While the actual scent type that Machine_A is able to emit will be determined by what particular scent or scents are physically installed in the machine, entering the scent information here will enable the central controller 102 to keep track of which machine is configured to which scent. This information may inform the machine-relatedness determination noted below.

In similar fashion, pull-down box 306 can be used to identify the particular location associated with Machine_A. While the actual location of Machine_A is determined by where the machine is physically located, entering the scent information here will enable the central controller 102 to keep track of where each machine is located. This information also may inform the machine-relatedness determination noted below.

Entry boxes 308 and 310 may identify, respectively, the desired scent cycle time and scent level percentage for Machine_A. Here, scent cycle time refers to the period of time during which one on-off cycle occurs while scent level percentage refers to the percentage of time during the cycle time in which the machine is turned ON (i.e., duty cycle). In some cases, data entries 308 and 310 indicate a base scent setting for the specified delivery unit that reflects an optimal setting for the particular unit. In some cases, the base scent setting for each machine may be determined automatically by the central controller 102. For example, the particular scent type and/or location as selected in pull-down boxes 304 and 306 may be pre-associated with a corresponding base scent setting, the information regarding which the central controller 102 may be configured to store or otherwise access.

Check box 312 may be used to indicate whether the associated scent delivery unit, in this case Machine_A, is enabled. For example, checking "NO" for check box 312 may effectively take Machine_A offline, allowing the central controller 102 to ignore any input concerning the activation of Machine_A. A user may not want a unit to be enabled, for example, during repair of the unit and/or during scent cartridge replacement.

Check box 314 may be used to indicate a mode of operation, or run mode, of the particular machine. Here, "automatic" may refer to the mode in which the machine is operated in accordance with the master schedule as maintained by the central controller 102. Accordingly, Machine_A in this case will activate and deactivate based on conflict-free command data generated by the central controller 102. Setting the run mode to "ON" or "OFF" may be akin to manual override of the machine. In other words, selecting ON for entry 314 will immediately activate the machine regardless of the activation/deactivation schedule contained in the master schedule. Likewise, selecting OFF for entry 314 will immediately deactivate the machine regardless of the master schedule. During a manual ON or OFF period, scheduled events to the contrary may not be permitted by the central controller 102. In other words, a manual control will have, under this scheme, priority over any previously or subsequently added scheduled events.

As with scheduled events, immediate requests for activation and/or deactivation may be sent by the central controller 102 as command data. In some cases, "automatic" may be a default setting for check box 314 to which the selection will revert back after a period of time. For example, any selections of either ON or OFF may reset back to "automatic" every day at midnight, thereby returning the machine to automatic, scheduled control. Accordingly, while disabling the machine via entry 312 and manually turning off the machine via entry 314 can both effectively take the machine offline, turning off the machine via entry 314 will allow it to automatically revert back to automatic mode after a period of time.

Referring again to the graphical window 300 in FIG. 3, pull-down box 316 may be used to indicate a group to which a particular machine may belong. As discussed further below in relation to the scheduling process, grouping multiple machines into a group may allow the user to quickly schedule a larger number of machines without having to enter a separate event for each machine. Alternatively, or additionally, a separate interface may be used to define various groups and the machines contained therein.

Pull-down box 318 may be used to input information regarding related units, which will be discussed further below. Alternatively, or additionally, an additional user interface may be provided to allow the user to choose which units are related. Entry box 320 may be used to input information regarding fail safe time, which will be discussed further below.

In some implementations, any authenticated user may access the window 300 and change the data corresponding to all or some of the GUI input elements in the window 300.

In other implementations, only an authenticated system administrator user can access the window 300 and change the data corresponding to all or some of the GUI input elements in the window 300. In these implementations, the other authenticated users may not be allowed to access the window 300, may be allowed to access the window 300 but may not be allowed to change the data displayed in the windows, or may be allowed to access the window 300 but may only change the data corresponding to a subset of the GUI input elements (e.g., can only change the run mode using check box 314).

FIG. 4 shows an example GUI that includes graphical windows 400 and 402 for creating scheduled events. In some implementations, any authenticated user that wishes to schedule a scenting event may interact with windows 400 and 402 using a user device 108 to schedule a scenting event. In other implementations, only an authenticated system administrator user is able to interact with windows 400 and 402 using a user device 108 to schedule a scenting event. In some implementations, any authenticated user that wishes to schedule a scenting event may interact with windows 400 and 402 using a user device 108 to provide scenting event schedule data to the central controller 102 but only authenticated system administrator users may interact with window 300 to provide unit-specific information to the central controller 102.

As illustrated, the graphical window 400 creates a scheduled event called "Schedule 1" (404) for Machine_A while the graphical window 402 creates a scheduled event called "Schedule 2" (424) for the same Machine_A. The user may create additional scheduled events as needed for Machine_A as well as other scent delivery units in the system 100 by opening a scheduled event interface for each new event desired. In this example, information pertaining to Machine_A corresponds to information entered for the same machine through interactions with the graphical window 300 in FIG. 3.

In further detail, by making selections in event type check boxes 406, 426, the user can indicate the desired type of a scheduled event. For example, a "calendar" type event can allow the user to choose days of the month as well as particular times of day during which machine or machines identified in pull-down boxes 410, 430 should be activated. A "weekly" type event, on the other hand, can allow the user to choose days of the week as well as particular times of day during which machine or machines identified in pull-down boxes 410, 430 should be activated. A weekly event, because it can be repeated week to week, may also be referred to as a recurring event. As illustrated in the graphical windows 400, 402, selecting the "weekly" option in entry 406 can cause the windows 400, 402 to display check boxes 412, 432 that allow the user to specify days of the week during which the machine or machines should be activated. The "on time" entries 414, 434 and "off time" entries 416, 436 indicate, respectively, the time at which the machine or machines should be activated and at which they should be deactivated. In some cases, each graphical window may include multiple on/off times to specify multiple activation periods in a single day.

In addition to allowing the user to specify operating conditions for individual machine or machines, group/unit check boxes 408, 428 can allow the user to specify operating conditions for a group of machines. For example, choosing "unit" in entry sections 408, 428 may cause pull-down menus 410, 430 to list all networked scent delivery units. As discussed further below with respect to FIG. 8, choosing "group" in entry sections 408, 428 may cause pull-down menus 410, 430 to instead list all groups of machines previously identified. This way, multiple scent delivery units associated with a group (e.g., a "Lobby Group" that includes all machines located in the lobby) may be quickly scheduled through a single scheduled event.

The bias setting entry boxes 418, 438 allow the user to input the desired scent level bias. A scent level bias of 0 indicates that the scheduled event should proceed at a scent level (e.g., duty cycle) associated with the base scent setting. A positive or a negative scent level bias indicates that the scheduled event should proceed at a scent level that is higher or lower, respectively, in relation to the scent level associated with the base scent setting. In some implementations, the numerical value of the scent level bias may correspond to a percentage change to the duty cycle associated with the base scent setting, which may be applied either arithmetically and/or geometrically as discussed above. In some implementations, the numerical value of the scent level bias may be an arbitrary value whose specific effects on the scent level may be determined by the central controller 102, or in some cases by the scent delivery units themselves, according to a pre-defined control logic. In some implementations, the numerical value of the scent level bias may correspond to a time value, for example a time change in seconds to be applied to a length of the ON cycle. Alternatively or additionally, the scent level bias may be applied to fan speed, nozzle pressure, compressor power, and/or other machine-specific parameters that may in other ways influence total number of scent particles released in an environment during a given amount of time.

Check boxes 420, 440 may be used to indicate whether or not the instant scheduled event is an anti-event, as will be discussed further below.

Figure 5:
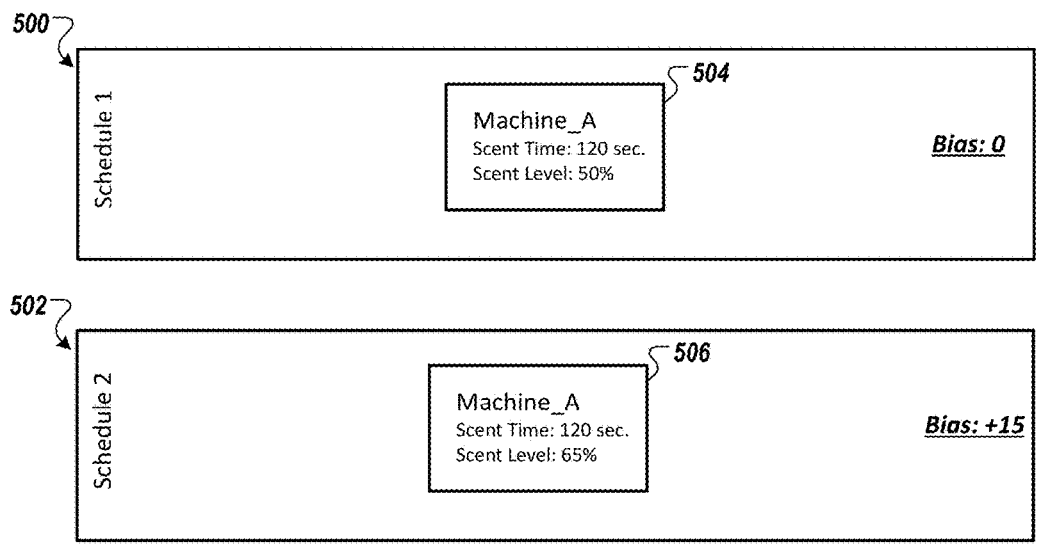
FIG. 5 is a graphical representation of scheduled events from FIG. 4.

FIG. 5 shows a graphical representation of two scheduled events 500, 502 as created through the exemplary GUI windows 400, 402 (FIG. 4). Reference is also made to information about Machine_A as mentioned in the example of FIG. 3. In some implementations, the central controller 102 is able to provide event-specific graphical representation to a user device 108 to enable the device 108 to display a GUI to the user that includes figures graphically depicting each scheduled event. Such figures enable a user to quickly, at-a-glance, see and compare the various scheduled events.

As shown in FIG. 5, scheduled events Schedule 1 and Schedule 2 include, respectively, event-specific machine data 504, 506. Representation of events 500, 502 also indicate the scent level bias that was included in the scheduled events, in this case 0 and +15, respectively. Here, the machine data 504, 506 represent information that the central controller 102 will use to generate appropriate command data. As such, data 504, 506 reflects an application of the scent level bias to the base scent setting. For example, the central controller 102 may generate command data for Machine_A, which has a base duty cycle of 50% (FIG. 3), that corresponds to a 50% duty cycle in Schedule 1 and a 65% duty cycle in Schedule 2. The base scent setting for Machine_A in either of the exemplary scenarios will remain unchanged (i.e., scent time of 120 sec. and duty cycle of 50%).

Figure 6:
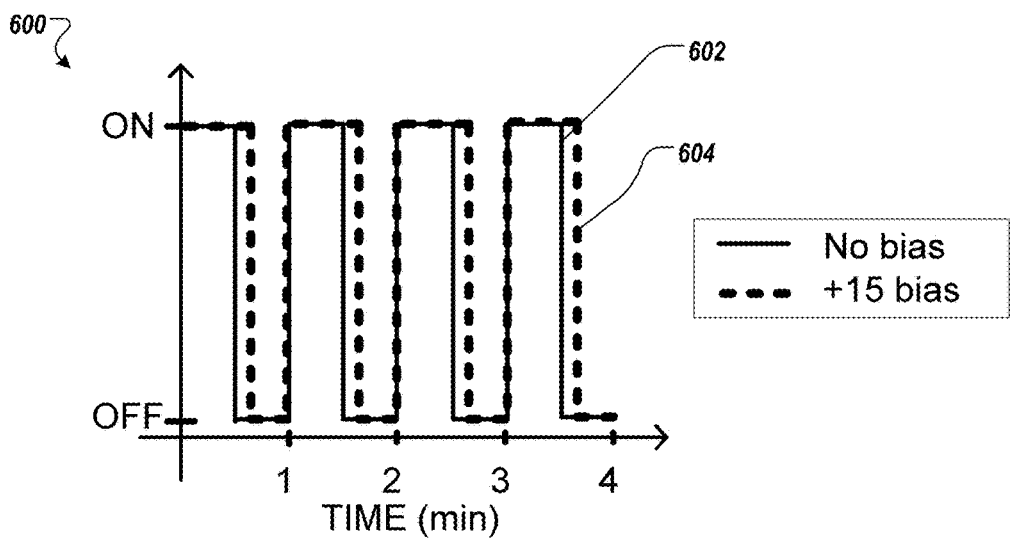
FIG. 6 illustrates duty cycles before and after a bias.

FIG. 6 shows a plot 600 illustrating duty cycle-based scent cycling that would occur during an activation period of Machine_A under Schedule 1 (602) and under Schedule 2 (604). As shown, a positive scent level bias has the effect of increasing the ON time for each cycle while decreasing the OFF time.

In some implementations, the central controller 102 may automatically add a period of rest after an activation period to, for example, allow any lingering scent to sufficiently dissipate before scent from the next event is emitted. For example, referring to Schedule 2 form FIG. 4, the central controller 102 may automatically add a rest period at 9 pm (e.g., 2 minutes) so that subsequent scenting events taking place in the same location are delayed. As such, a scent event scheduled to run from 9 pm to 11 pm in the same location as Schedule 2 may be revised to instead run from 9:02 pm to 11 pm. This way, the added rest time may allow scent particles from Schedule 2 to sufficiently dissipate from the scenting environment before scent particles from the next scheduled event are introduced into the same space.

A length of the automatically added rest period, as described above, may vary according to a multitude of factors, including, but not limited to, scent type, dissipative properties of scent particles, length of activation period, type of room being scented, etc. Based on one or more such factors, the central controller 102 may be configured to automatically calculate the appropriate rest period using a predefined algorithm. For example, a small room with high foot traffic (e.g., lobby) may require less rest period than a large open space (e.g., ballroom). Similarly, a short activation period may require less rest period than a long activation period. Additionally, or alternatively, the central controller 102 may be configured to automatically calculate and implement the appropriate length of rest based on the scent level bias of the preceding event. For example, a scenting event operated under a high positive bias may require a longer rest period compared to an event operated under a high negative bias.

Figure 7:
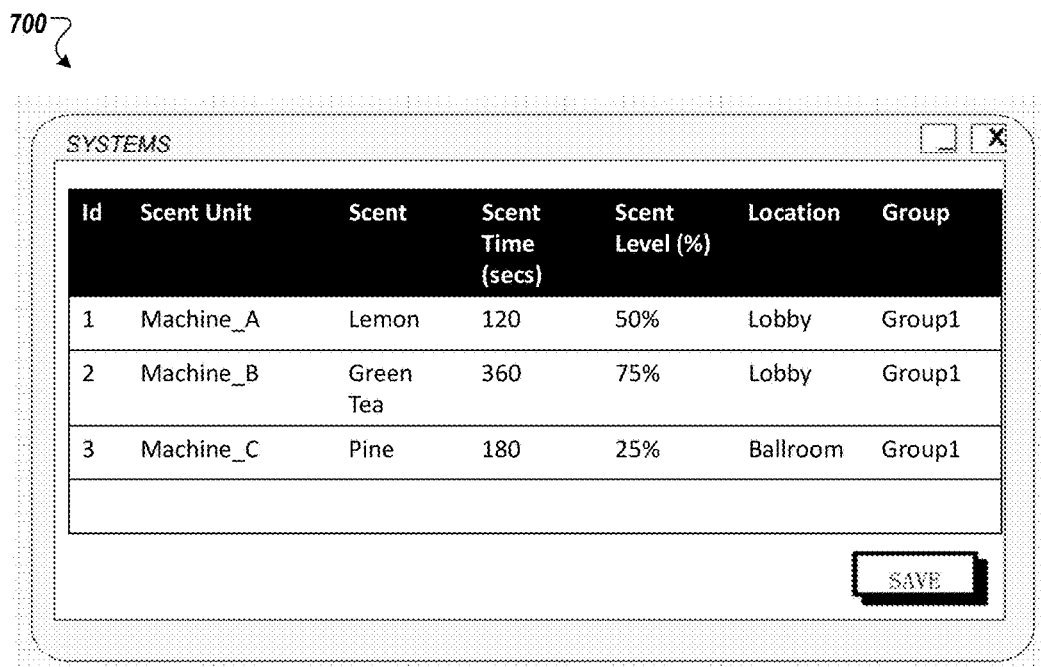
FIG. 7 shows a sample graphical window illustrating multiple scent delivery units in a group.

Referring to FIG. 7, a GUI window 700 shows multiple scent delivery units that may be associated with a single group, in this case Group1. Referring also to FIG. 8, windows 800, 802 illustrate how two scheduled events, Schedule 1 and Schedule 2, may be created by designating groups of machines, instead of individual machines as illustrated in the example of FIG. 4. Each scent delivery unit may be associated with multiple groups.

To create scheduled events for groups, entries 804-840 in graphical windows 800, 802 may be completed in much the same manner as described above with respect to windows 400, 402 in FIG. 4. Check boxes 808, 828 should, however, indicate that a "group" is being selected instead of a "unit." Making this selection in boxes 808, 828 will cause pull-down boxes 810, 830 to list all groups as identified by the central controller 102. In this example, "Group1" may be chosen in entries 810, 830 to indicate that all machines listed in window 700 should be controlled for this scheduled event. The bias setting entry 818, 838 may be completed as before to indicate the desired scent level bias for all machines in the group.

Figure 9:
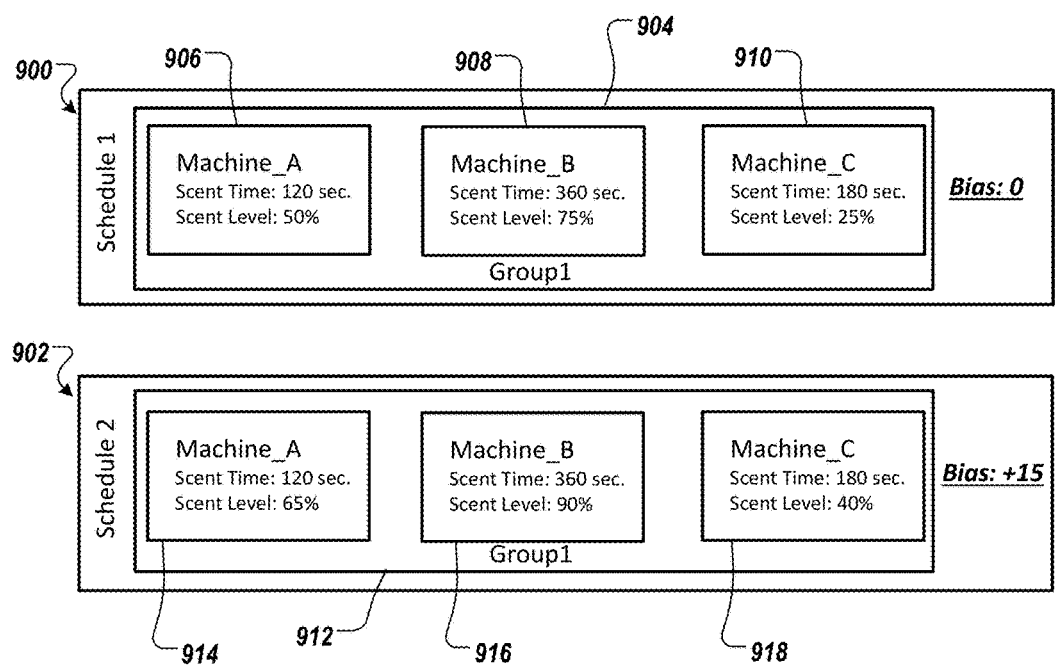
FIG. 9 is a graphical representation of scheduled events from FIG. 8.

FIG. 9 shows a graphical representation of two scheduled events 900, 902 as created through the exemplary GUI windows 800, 802 (FIG. 8). Reference is also made to information about individual units of Group1 as given in FIG. 7.

As shown in FIG. 9, scheduled events Schedule 1 and Schedule 2 include, respectively, event-specific group data 904, 912, each of which contains event-specific machine data 906-910 and 914-918, respectively. Representation of events 900, 902 also indicate the scent level bias that was included in the scheduled events, in this case 0 and +15, respectively. Here, the group data 904, 912 represent information that the central controller 102 will use to generate appropriate command data. As such, the group data 904, 912 reflect an application of the scent level bias to the base scent settings of each machine in the group.

Figure 10:
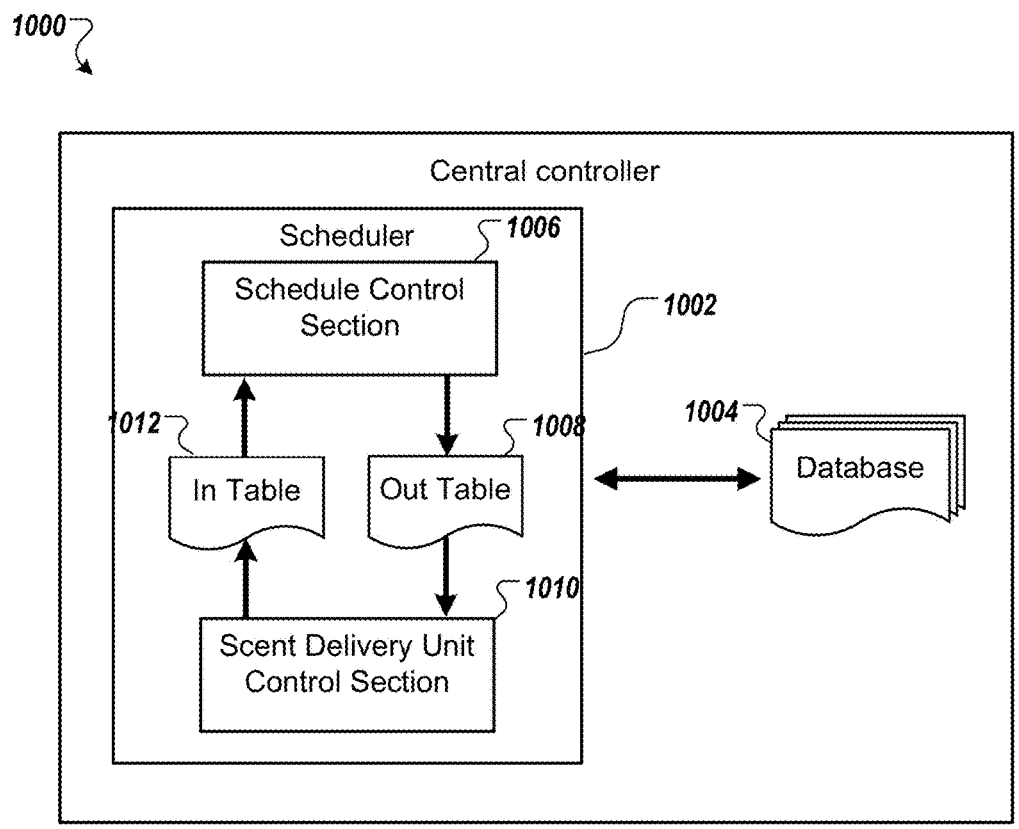
FIG. 10 is a block diagram of an implementation of a central controller.

Referring to FIG. 10, a block diagram 1000 illustrates an exemplary implementation of the central controller 102 (FIG. 1). As shown, exemplary central controller may be largely divided into two components: scheduler 1002 and database 1004. Here, the scheduler 1002 is mainly responsible for the scheduling and controlling of individual scent delivery units while the database 1004 stores or otherwise makes accessible data pertaining to each scent delivery unit in the system. For example, contents of the window 300 (FIG. 3) and window 700 (FIG. 7) may be stored and maintained in the database 1004.

In further detail, the scheduler 1002 can include a schedule control section 1006 and a scent delivery unit control section 1010. In this implementation, the schedule control section 1006 is configured to receive the desired scheduling information from the user, e.g., via one or more scheduled events, and communicate with the database 1004 as needed to retrieve data pertaining to the scent delivery unit referred to in the one or more scheduled events. For example, in response to the entry of the scheduled event shown in graphical window 400 (FIG. 4), the scheduler control section 1006 may query the database 1004 to find out the network location of Machine_A.

The schedule control section 1006 may be configured to perform a bias-applying process, such as process 200 (FIG. 2), in order to generate command data that changes the instant scent level of scent delivery units without changing their base scent settings. In one implementation, the generated command data may be in the form of a list of instructions for each scent delivery unit in the networked system 100. For example, in reference to FIG. 4, the list of instructions for Machine_A under Schedule 1 may include (i) turning on at 9:30 am and (ii) turning off at 2:30 pm. Similarly, referring again to FIG. 4, the list of instructions for Machine_A under Schedule 2 may include (i) turning on at 3:00 pm under a +15 scent level bias and (ii) turning off at 9:00 pm. The schedule control section 1006 may then output this list of instructions to an out table 1008. The out table 1008 can be configured to store the updated list of instructions for each machine in the system. The out table 1008 may be updated following the addition, deletion, and/or revision of a scheduled event. Alternatively, or additionally, the schedule control section 1006 may update the out table 1008 periodically according to a pre-determined schedule (e.g. every minute) regardless of whether any changes were made to the scheduled events.

In another implementation, the out table 1008 may include real-time instructions for the scent delivery units. That is, the list of instructions may simply instruct the machine to, for example, turn on and start operating at the given cycle time and duty cycle. In response, the machine may continue to operate at the given duty cycle until a subsequent instruction received from the out table 1008 instructs the machine to turn off. In this implementation, the scent delivery units may require minimal intelligence and functionality.

The scent delivery unit control section 1010 may be configured to directly implement a communication protocol between the central controller and the individual scent delivery units. For example, the scent delivery unit control section 1010 may be configured to simply read off instructions from the out table 1008 and broadcast them one by one to each of the network-controlled scent delivery units. In some cases, the scent delivery unit control section 1010 may be configured to verify proper data communication by receiving verification signals from the individual scent units. Such verification signals may be received and stored in an in table 1012. The in table 1012 may send or otherwise make accessible the verification information to the schedule control section 1006, such that a user may receive real-time status updates of each machine out in the field.

As noted above, a master schedule can refer to an aggregate of all scheduled events and may be maintained by the central controller 102. In one implementation, master schedule data is updated by user input at unpredictable times (e.g., when the user decides to add/update/remove a scheduled event). Updated master schedule data may then be processed by the schedule control section 1006 in real-time (e.g., once every few seconds), in response to and upon detection of user input of a new or modified scheduled scenting event, or at predetermined time intervals (e.g., once every 5 minutes) to generate/update non-conflicting machine-specific instruction tables. The machine-specific instruction tables are a list or grouping of instructions with corresponding execution time information for a specific machine. The machine-specific instruction tables for all machines in the system may be aggregated into the out table 1008. The instructions for a corresponding machine's operation included in a particular machine-specific instruction table may indicate operations that need to be performed by the machine over a relatively long period of time (e.g., a day, a week, or a month).

In one implementation, the scent delivery unit control section 1010 receives the out table 1008, which contains the non-conflicting machine-specific instruction tables, and sends out each machine instruction (e.g., "turn on" instruction) at its appropriate time to each respective machine based on the out table 1008 (e.g., by processing the table). The delivery of an instruction may occur in real-time (e.g., a "turn on" instruction is sent in real-time, which results in the machine turning on in response to and upon receipt of the instruction). This implementation allows scent delivery units with little intelligence to be used. However, this implementation may also have greater sensitivity to connection failures, given that it may require a relatively continual and uninterrupted connection between the central controller and the units to operate properly.

In an alternative implementation, delivery of instructions from the scent delivery unit control section 1010 may occur ahead of time (e.g., a "turn on at 6 pm" instruction being sent at 5 pm). In some cases, the scent delivery unit control section 1010 may simply send the non-conflicting machine-specific tables (or the updated portions of the same) to each of their respective machines for processing. In these cases, the machines are intelligent units able to process the tables with their own internal and synchronized clocks. This implementation may be less sensitive to connection errors because the instructions generally do not need to be continually sent in real-time for proper operation. This implementation, however, requires more intelligent scent delivery units that have additional processing capabilities to process the instructions at their appropriate times in synchronicity with the other scent delivery units (e.g., scent delivery units that each have their own clock that may include circuitry to synchronize the clock with the clocks of the other scent delivery units and that each have the processing capabilities to interpret and execute more complex received instructions).

In some implementations, updated master schedule data may be processed by the schedule control section 1006 in real-time (e.g., once every few seconds) in response to and upon detection of user input of a new or modified scenting event, or at predetermined time intervals (e.g., once every 5 minutes) to generate/update a second version of the master schedule that is non-conflicting. Notably, in some implementations, this second version may be saved as separate data from the conflicting master schedule data to allow the conflicting master schedule data to be preserved intact for subsequent processing based on new user input. In other implementations, the second version may overwrite the master schedule data and become a new master schedule data used for future processing based on new user input. These implementations, however, may be less preferable in that they may limit the ability to recover the original user-inputted scenting event data when conflicts subsequently change (e.g., go away) as a result of subsequent user input.

In some implementations, the updated, non-conflicting master schedule data may be sent directly by the scent delivery unit control section 1010 to each scent delivery unit for processing. Each scent delivery unit in this implementation has intelligence to directly process the master schedule at clock times that are synchronized with that of the other units.

In some implementations, the schedule control section 1006 may process the updated, non-conflicting master schedule data (i.e., the second version of the master schedule data) to generate non-conflicting machine-specific instruction tables that are subsequently sent to each respective machine. Here, no conflict-resolving processes are required to generate the machine-specific instruction tables since the master schedule itself has been updated to be conflict-free. As described above, such machine-specific instructions may be sent out in real-time to less intelligent scent delivery units or may be sent out ahead of time to more intelligent scent delivery units.

Figure 11:
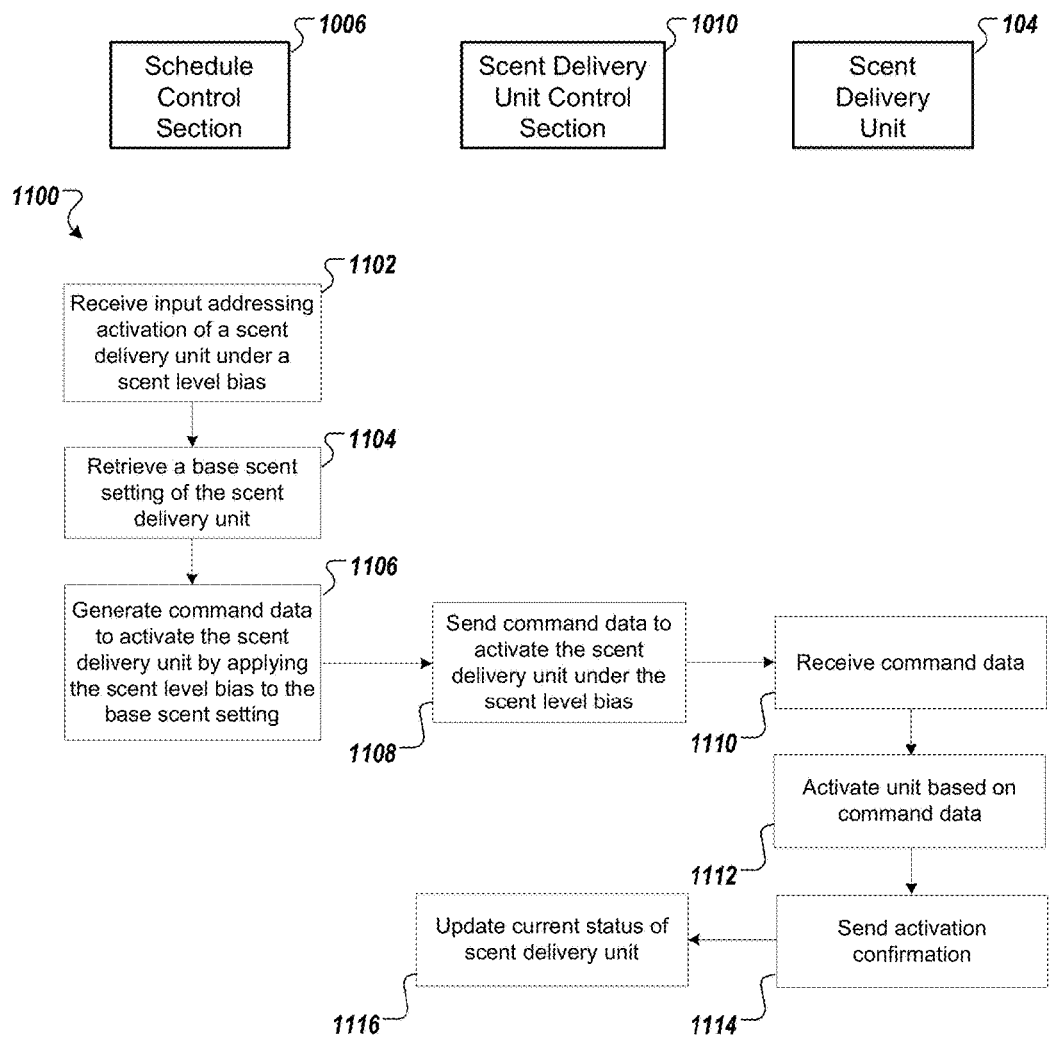
FIG. 11 is a flow chart of a process for activating a scent delivery unit in relation to the central controller of FIG. 10.

FIG. 11 is a flowchart of an example process 1100 in which the central controller may command scent delivery to activate under a scent level bias. While process 1100 may be implemented by various systems, explanation of the exemplary process 1100 is given in relation to the controller described in FIG. 10.

The schedule control section 1006 is configured to receive input addressing the desired activation of a scent delivery unit under a scent level bias (1102). For example, as illustrated in graphical window 402 (FIG. 4), a scheduled event that includes the desired scent level bias (i.e., bias setting), may be received by the schedule control section 1006.

Based on the received input and the retrieved base scent setting (1104), the schedule control section 1006 generates command data to activate the scent delivery unit by applying the received scent level bias to the retrieved base scent setting (1106).

The generated command data is subsequently sent to the scent delivery unit by the scent delivery unit control section 1010 (1108). In some cases, the command data may be in the form of network packets or other suitable data formats that can be communicated across the network 106. The one or more scent delivery units 104 are configured to receive such data (1110) and operate (i.e., turn on or off) based on the received data (1112). In some implementations, the one or more scent delivery units may send a confirmation signal back to the scent delivery unit control section 1010 (1114), to indicate, for example, that the sent data has been properly received and/or that the machines are functioning properly. The scent delivery unit control section 1010 may then update the current status of each machine by, for example, appropriately populating the in table 1012 (1116). In some cases, the command data may be in the form of a signal that is a waveform and may include multiple transitions in signal level that correspond to changes in the on/off state of the corresponding scent delivery unit. In some cases, the signal may be a pulse that corresponds to a change in the on/off state of the corresponding scent delivery unit.

Figure 12:
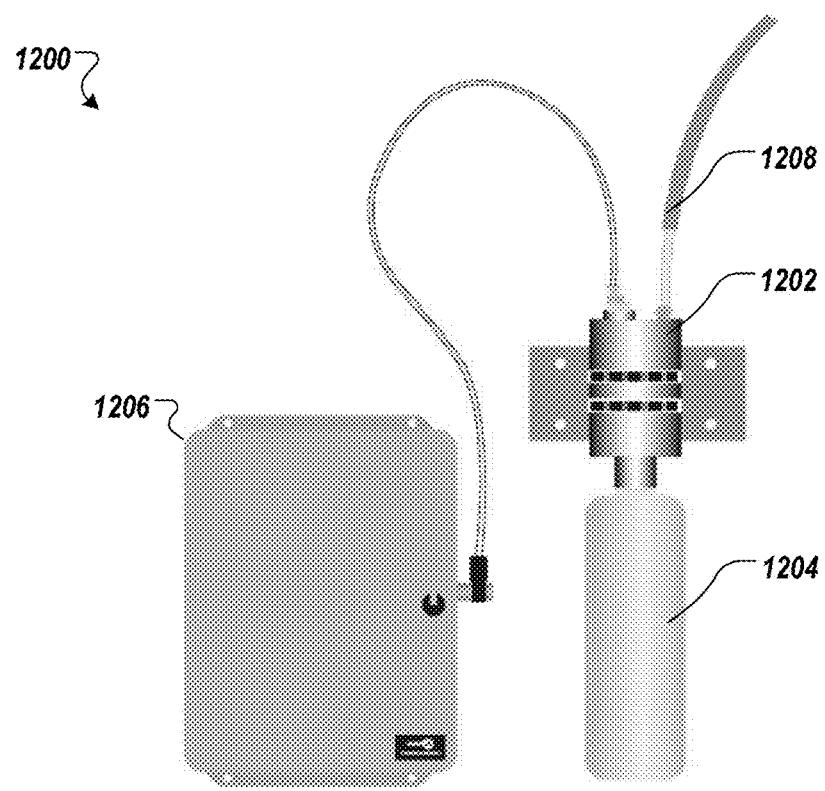
FIG. 12 is an implementation of a scent delivery unit.

FIG. 12 shows an exemplary scent delivery unit 1200. The scent delivery unit 1200 may be used as a standalone system, or may be used as part of the networked scent delivery system 100. Briefly, the scent delivery unit 1200 includes a diffusion head 1202 that is mounted on a cartridge bottle 1204. Scented liquid is stored within the bottle 1204 and can be atomized into the atmosphere via the head 1202. The diffusion head 1202 may comprise a venturi-type atomizer.

In one implementation, each scent delivery unit 104 includes a scent reservoir and an atomizing device in fluid communication with the scent reservoir. In one example, the scent reservoir is a cartridge bottle containing scented liquid, for example a fragrant oil mixture having a desired scent for the particular scent delivery unit 104. The atomizing device can be, for example, a venturi-type atomizer that uses a high velocity airstream generated within a control unit 1206 to draw in and atomize the liquid in the cartridge bottle 1204 into small particles (e.g., under 10 microns in diameter) that can be dispersed into the air via a nozzle 1208. The control unit 1206 may include a network receiver or the like to receive command data sent by the central controller 102 (FIG. 1).

Figure 13:
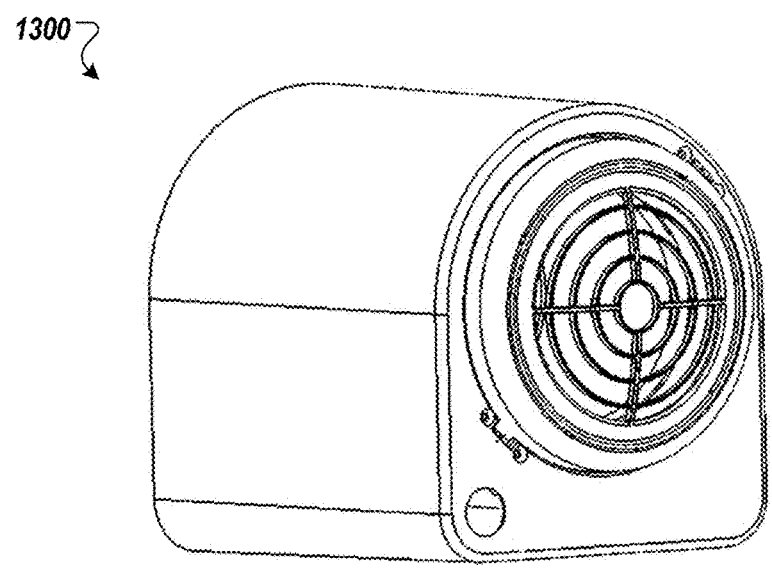
FIG. 13 is another implementation of a scent delivery unit.

FIG. 13 shows an alternative scent delivery unit 1300. The scent delivery unit 1300 may be a canister type machine that includes a wicking structure impregnated with fragrance material. Airflow through the scent delivery unit 1300, for example generated by an on-board fan, can help evaporate and release the fragrance into the environment. Control electronics, network receiver, and other electrical/mechanical components may be included within a casing of the scent delivery unit 1300.

Scent delivery units 1200 and 1300 represent just two of many different types of scent delivery technologies that may be used with the scent delivery system 100. Other types of scent delivery technologies may include evaporative systems based on natural convection. Evaporative systems may use scents from fragrance carriers such as liquid fragrance oil suspended in porous media including, but not limited to, woven/non-woven fabrics, papers felts, wood-like materials, porous plastics, foams, sponges, screens and wool-like materials. In some cases, fragrant compounds used in evaporative systems may be incorporated in semi-solids such as gels or may be absorbed into the intermolecular structure of nonporous materials such as plastic beads, fibers, or films. Evaporative systems may release scent when fragrance carriers/evaporative media contained therein are exposed to air. Scent delivery technologies may also include forced convection-type devices that rely on forced convection produced by fans or directed compressed air (e.g., from pumps or pressurized tanks) to enhance the release of scent from the above-noted evaporated media. Alternatively or additionally, heat energy (e.g., radiant heat from a candle or convective heat from a heated blower) may be incorporated to increase the rate of fragrance evaporation. Scent delivery technologies may also include direct diffusion-type devices where fragrance compounds are directly diffused into the air through various forms of atomizers to produce a wide range of desired particle sizes. An atomizer may be in the form of hydraulic spray nozzles configured to directly release high-velocity liquids, liquid-liquid impinging atomizers configured to collide liquid streams, and air-liquid impinging atomizers such as bubble tanks, airblast atomizers, prefilming atomizers, and venturi-type atomizers. An atomizer may be a mechanical atomizer that relies on spinning discs or vibrating structures, for example, to deliver scent. For example, piezoelectric transducers may be used to atomize liquid oils via ultrasonic surface wave effects, or through the use of microscopically perforated vibrating mesh (VMT). In some cases, high voltage can be used in an electrospray device, where electrostatic forces can cause the expulsion and dispersal of tiny volumes of liquid from a single fine orifice or a brush like structure of multiple points. Notably, any scent delivery unit is configured to deliver scent at a variable scent level by being turned on and off successively according to a variable duty cycle if it delivers scent at a variable scent level by being turned on and off successively according to a variable duty cycle, regardless of whether it is specially configured for such operation or whether it is instead designed for use without duty cycle variations.

A number of implementations have been described. Nevertheless, it will be understood that various modifications may be made without departing from the spirit and scope of the disclosure.

For example, while the above-described implementations assume a single unit or machine corresponds to a single, physical piece of equipment that produces a single scent (e.g., Unit A may correspond to a single, physical scent delivery machine that includes a single cartridge bottle containing a single Pineapple scent), it should be understood that in other implementations a single, physical piece of equipment may be configured to produce many different scents, either concurrently and/or serially, and, therefore, may correspond to multiple different of the above-described machines or units (e.g., Unit A corresponds to the first cartridge bottle of a single physical piece of equipment that contains a Pineapple scent and Unit B corresponds to a second cartridge bottle of the same single physical piece of equipment that is configured to produce a leather scent). Accordingly, in implementations in which a single, physical piece of equipment may deliver different scents (e.g., through different cartridges), the single, physical piece of equipment may be treated as if it were multiple of the above-described different units or machines. In such implementations, a machine may refer to the single, physical piece of equipment while a unit may refer to each of the corresponding above-described different units or machines that may be collocated, sharing the same power and same HVAC, emitting a different, single scent, etc. Additionally, while the above-described implementations assume a scent delivery unit or a machine includes one or more of the above-noted scent delivery technologies, it should be noted that the scent delivery unit or machine may correspond to any element, including hoses, nozzles, and orifices, that can deliver scent in accordance with a schedule maintained by the central controller.

In another implementation, a scent level bias may result in command data that reflects a change to both the cycle time as well as the duty cycle associated with a base scent setting of a particular scent delivery unit. That is, applying a scent level bias to the base scent setting of a particular scent delivery unit may include activating the unit under an altered duty cycle as well as under an altered cycle time. For example, a scent delivery unit having a base cycle time of 600 seconds and a base duty cycle of 50% might typically operate, without any scent level bias, by successively turning on for 300 seconds and turning off for 300 seconds. In response to a scent level bias of +45, the command data for activating the unit may then indicate that the unit should operate under a cycle of 570 seconds of ON time and 30 seconds of OFF time, reflecting in this case increasing the duty cycle to 95% while keeping the cycle time the same. In some cases, however, the user may prefer that this unit not stay on continuously for more than, as an example, 540 seconds (i.e., maximum ON time), for example to prevent overheating. In such a case, the command data may be adjusted accordingly to take into account both the +45 bias as well as the 540 second maximum ON time. To achieve this, the command data may indicate that the unit should operate under a cycle of 540 seconds of ON time and 28.4 seconds of OFF time, reflecting in this case increasing the duty cycle time to 95%, as before, but also simultaneously decreasing the cycle time from 600 seconds to 568.4 seconds to satisfy the maximum ON time requirement.

Similarly, in some cases, the user may prefer that the unit's ON time be longer than, as an example, at least 60 seconds (i.e., minimum ON time), for example to give the machine sufficient time to emit a discernible amount of fragrance into the environment. In such a case, applying −45 scent level bias to above example may result in command data indicating that the unit should operate under a cycle of 30 seconds of ON time and 570 seconds of OFF time, reflecting in this case increasing the duty cycle to 95% while keeping the cycle time the same. To satisfy both the desired scent level bias and the minimum ON time, the command data may then indicate that the unit should operate under a cycle of 60 seconds of ON time and 1140 seconds of OFF time, reflecting in this case decreasing the duty cycle time to 5%, as before, but also simultaneously increasing the cycle time from 600 seconds to 1200 seconds to satisfy the maximum ON time requirement.

In some implementations, the user may prefer that the scent delivery unit operate in accordance with minimum/maximum OFF time. In such cases, the cycle time may also be similarly varied as described above with respect to minimum/maximum ON time.

In another implementation, the central controller 102 can include pre-determined logic to prevent scent delivery units that are "linked" or "related" to each other from being activated simultaneously. A scent delivery unit, or machine, may be said to be related (or linked) to another if a user makes a prior determination, for example, that these two particular machines should not be activated at the same time regardless of information contained in the scheduled events.

In an example scenario, a systems administrator may determine that scent delivery unit A and scent delivery unit B, each of which is configured to deliver a different scent to a same room, should not be activated at the same time in order to prevent overscenting the room and exposing its occupants to unpleasantly high levels of scent. In this case, the systems administrator may indicate to the central controller 102 that units A and B are related to each other. The pull-down box 320 (FIG. 3) may list all available scent delivery units that the systems administrator may designate as being related. Once units A and B are designated as being related, the central controller 102 may be configured to prevent conflicting events from proceeding as scheduled. An example of a conflicting event could be where a first scheduled event indicates that unit A should be activated every Monday through Wednesday from 9:00 am to 5:00 pm while a second scheduled event indicates that unit B, which is related to unit A, should be activated every Wednesday through Friday from 3:00 pm to 10:00 pm. In this case, the two events may be said to be in conflict because an overlapping activation period occurs on every Wednesday from 3:00 pm to 5:00 pm.

In some implementations, in addition to or as an alternative to the system administrator directly indicating which machines are related, the central controller 102 may automatically identify any units that, for example, share a location as being related. For example, the central controller 102, upon receiving or otherwise accessing information that units A and B are both located in the same room, may automatically determine that units A and B are related to each other. In some implementations, the system administrator may manually set a preference with the central controller 102 that instructs the central controller 102 to perform an automatic relatedness determination.

While the above example discloses an automatic relatedness determination being performed by the central controller 102 based on determining that two units are collocated, the automatic relatedness determination performed by the central controller 102 (or the manual determination of the system administrator) may take into account one or more other factors in addition to or as an alternative to unit collocation. For example, scent delivery units that emit incompatible scents (e.g., scents that are not pleasant when smelled at the same time) may be defined or identified as being related. In another non-limiting example, scent delivery units that share a common power supply may be defined or identified as being related, for example, to prevent the common power supply from being overdrawn. In yet another non-limiting example, scent delivery units that are installed in different locations but otherwise emit scent to a same location (e.g., via the HVAC system) may be defined or identified as being related. In some cases, multiple machine-specific factors may need to be considered to indicate relatedness. For example, two machines may be said to be related if they share the same location but are configured to emit a different scent, or alternatively the same scent.

In another implementation, the central controller 102 may allow a user to schedule an anti-event in much the same way that a regular scenting event may be scheduled, with the anti-event capable of having priority over regular events. This may be desirable, for example, if the user wishes to schedule ahead of time one or more periods of time during which a particular location within the scenting environment will not be subjected to any scent delivery. In other words, the user might want to establish a kind of a "scent exclusion period" for certain scent delivery unit (or units) that may be associated with a particular location. It may also be desirable to schedule such a scent exclusion period, which also may be referred to as an anti-event, without having to alter any of the multiple scheduled events that may happen to address scent delivery directed to the time and location in question. To this end, the central controller 102 may be configured to generate command data to create such a scent exclusion period in accordance with pre-determined logic without having to alter pre-existing, or subsequently entered, scenting events.

One difference between an event and an anti-event may be that the event is configured to schedule a period of activation for a machine while the anti-event is configured to schedule a period of non-activation. In this way, a user may be able to use anti-events to quickly and easily schedule ahead a scent exclusion period during which certain machine or machines should not activate, regardless of other scheduled events that may indicate otherwise. Check boxes 420, 440 (FIG. 4) may be used for this purpose. Additionally, if scent exclusion is no longer desired, a user may be able to revert back to control via the regular scenting events by simply removing the anti-event.

In another implementation, each scent delivery unit may be associated with a fail safe time that indicates a maximum amount of time that a machine will remain on in the event of, for example, a communication failure that prevents the unit that has turned on from receiving a turn off signal. As a result, overscenting by any particular machine due to a lost signal within the network may be prevented. In some cases, the fail safe time for each machine may be determined by the user through, for example, the fail safe entry boxes 320 (FIG. 3). Alternatively, or additionally, the fail safe time for each machine may be determined automatically by the central controller 102 according to a pre-defined algorithm (e.g., fail safe time is proportional to the size of the room in which the corresponding scent delivery unit is located).

As noted above, the central controller 102 is configured to generate and send command data to control each scent delivery unit. In some cases, the fail safe time for each machine, defined manually and/or automatically as described above, may be sent to the machine every time that a turn on command is sent. For example, a command to turn on a particular machine may be sent along with fail safe time data of 10 minutes. In turn, the receiving machine may be configured to respond to the fail safe time of 10 minutes by subsequently turning itself off 10 minutes after turning on if no turn off command is received by that time. That is, if the central controller 102 sends a turn off signal 1 minute after having sent the turn on signal (e.g., as part of an activation period that includes multiple cycles of on/off commands) but the turn off signal becomes lost or is otherwise never received by the machine, the machine will nevertheless turn off automatically according to the fail safe time at the 10 minute mark if no other turn off signals are received by then from the central controller 102. If the first turn off signal is never received by the machine, but a subsequent turn on signal with its own fail safe data is received before the end of the previous fail safe time period, then the machine may be configured to turn off automatically according to the new fail safe time. If the subsequently received turn on signal does not include a new fail safe time, the machine may revert back to and newly apply the previously received fail safe time. Because the fail safe time data is sent along with the command data, the fail safe time may be updated as needed based on user preference and/or machine-specific factors. In some cases, the fail safe time may be sent periodically to the machine along with just some of the command data sent to said machine. In some cases, the central controller 102 may be configured to send only turn on signals to each scent delivery unit without sending any turn off signals. In such a case, the fail safe time may be sent along with each turn on signal so that each unit will turn off by itself after a desired amount of time without having to receive an explicit turn off signal from the central controller 102. In such a case, a turn off signal sent by the central controller 102 may serve as a redundant process for ensuring that the scent delivery units will not overscent. In some cases, the fail safe time period may be shorter than the desired on period. In such a case, the central controller 102 may adjust and/or prompt the user to adjust the fail safe time to be at least longer than the desired on period.

In another implementation, the central controller 102 may be configured to introduce asynchronicity to the start times of multiple scent delivery units that are scheduled to activate at the same time. As a result, multiple command data that may otherwise have been transmitted simultaneously to multiple machines may instead be spread out in time. Such artificially introduced asynchronicity may help prevent overloading the network and/or reduce power surges that may occur from multiple machines being commanded to turn on simultaneously.

In one implementation, the central controller 102 may achieve the desired asynchronicity by adding a different skew parameter to the start time of each unit originally scheduled for a synchronous start. For example, given a predefined global skew parameter G (e.g., 0.1 seconds), the central controller 102 may add a different multiple of the global skew parameter (e.g., 0×G, 1×G, 2×G, 3×G, etc.) to each of multiple machines that have been scheduled by the user to start scenting at the same time (e.g., 4:00 pm). This way, each of the machines scheduled by the user to activate at 4:00 pm will start at a slightly different time.

In another implementation, the central controller 102 may be configured to compensate for unintended asynchronicity in multiple machines that are configured to behave synchronously, especially under a duty cycle-based control scheme. As noted above, precise control of scent levels may be achieved by turning each scent delivery unit on and off successively in accordance with a specified duty cycle during said unit's time of activation. Under this control scheme, a cycle time of each scenting unit may refer to the period of time during which one on-off cycle occurs for a given machine while the duty cycle would refer to the percentage of time during each cycle time during said machine is releasing scent. By synchronizing the start of on-off cycles across multiple machines, the perception of scent variation within a scenting environment may be maximized. In other words, if there are multiple machines that are configured/programmed to be synchronized, the central controller 102 may adjust the generation and/or transmission of command data to ensure that all on-off cycles for the three machines occur at the same time. For example, if three machines A, B, and C are scheduled to activate at 4:00 pm based on a cycle time of 10 minutes and a duty cycle of, respectively, 50%, 40%, and 30%, then the central controller 102 may generate command data, as discussed above, to turn on machines A, B, and C at 4:00 pm and to subsequently turn off the machines at 4:05 pm, 4:04 pm, and 4:03 pm, respectively. During the next on-off cycle, the central controller 102 may generate command data to turn on machines A, B, and C at 4:10 pm and to subsequently turn off the machines at 4:15 pm, 4:14 pm, and 4:13 pm, respectively. This cycling process will typically continue until the scheduled deactivation time, with all three machines starting each cycle at the same time. In some cases, however, a synchronously scheduled machine may drift from the synchronized schedule. For example, machine B in the above scenario may start at a delayed start time of 4:01 pm due to a communication error, and this 1 minute delay may be propagated to each subsequent on times (e.g., 4:11 pm, 4:21 pm, etc.). Upon identifying the delay in machine B, under the synchronous start implementation, the central controller 102 may also delay by 1 minute the start of each cycle for machines A and C. This way, machines A, B, and C will continue to turn on at the same time to achieve the desired scenting effect, regardless of any individual machine delays that may have otherwise broken up the scheduled synchronicity. In one implementation, the central controller 102 may be configured to identify delays in the machines by accessing the corresponding verification information in the in table 1012.

Accordingly, other implementations are within the scope of the following claims.

What is claimed is:

1. A scent delivery system comprising:
   a plurality of scent delivery units, wherein each scent delivery unit is configured to deliver scent at a variable scent level by being turned on and off successively according to a variable duty cycle, wherein the variable duty cycle includes an "on" time duration and an "off" time duration, and wherein each of the plurality of scent delivery units is associated with a corresponding base scent setting; and
   a central controller configured to control the plurality of scent delivery units, wherein controlling the plurality of scent delivery units includes:
   defining a group of scent delivery units from the plurality of scent delivery units,
   receiving input indicating a scent level bias to be applied to the base scent setting of each scent delivery unit included in the group for a particular activation period, and
   generating command data for each scent delivery unit included in the group, wherein the command data is generated by applying the scent level bias to the base scent setting using a predefined algorithm, wherein the predefined algorithm modifies the base scent setting using the scent level bias, and wherein when the command data is received at a scent delivery unit included in the group, the corresponding scent level of the scent delivery unit is varied based on the generated command data.

2. The scent delivery system of claim 1, wherein the central controller is configured to vary the duty cycles that are associated with each scent delivery unit in the defined group of scent delivery units based on the generated command data, wherein the predefined algorithm includes an arithmetic function.

3. The scent delivery system of claim 1, wherein the central controller is configured to vary the duty cycles that are associated with each scent delivery unit in the defined group of scent delivery units based on the generated command data, wherein the predefined algorithm includes a geometric function.

4. The scent delivery system of claim 1, wherein the central controller is configured to vary the duty cycles that are associated with each scent delivery unit in the defined group of scent delivery units based on the generated command data, wherein each scent delivery unit in the defined group corresponds to a parameter, and wherein the parameter indicates a scent type that is associated with each scent delivery unit included in the group of scent delivery units.

5. The scent delivery system of claim 1, wherein the central controller is configured to vary cycle times that are associated with each scent delivery unit in the defined group of scent delivery units based on the generated command data.

6. The scent delivery system of claim 1, wherein the scent delivery units are configured to turn on and off successively according to a variable duty cycle that ranges between 5% and 95%.

7. The scent delivery system of claim 1, wherein the central controller is configured to vary the base scent setting that is associated with each scent delivery unit in the defined group of scent delivery units based on the generated command data, wherein each scent delivery unit in the defined group corresponds to a parameter, and wherein the parameter indicates a scent type that is associated with the scent delivery unit.

8. The scent delivery system of claim 1, wherein the scent delivery units are configured to deliver scent at a variable scent level by varying one or more of fan speed, nozzle pressure, and compressor power of each scent delivery unit, and wherein, based upon a variation in the scent level bias, the central controller sends command data that indicates a corresponding variation to a corresponding one or more of fan speed, nozzle pressure, and compressor power of the scent delivery units.

9. The scent delivery system of claim 1, wherein the central controller generates and sends a signal to multiple scent delivery units, the signal reflecting a duty cycle that reflects power characteristics to be applied in successively turning the scent delivery units on and off.

10. The scent delivery system of claim 1, wherein the central controller generates and sends a signal to multiple scent delivery units, the signal being a pulse that corresponds to the multiple scent delivery units being turned on or off.

11. The scent delivery system of claim 1, wherein the central controller generates and sends a different signal to each of at least two scent delivery units, each different signal reflecting a duty cycle that reflects power characteristics to be applied in successively turning a corresponding scent delivery unit on and off.

12. The scent delivery system of claim 1, wherein the central controller generates and sends signals to each of at least two scent delivery units, wherein the signals sent to a first of the at least two scent delivery units vary in time relative to the signals sent to a second of the at least two scent delivery units, and wherein the signals include pulses that correspond to the corresponding scent delivery unit being turned on or off.

13. A method for delivering scent comprising:
providing a plurality of scent delivery units, wherein each scent delivery unit is configured to deliver scent at a variable scent level by turning scent delivery units on and off successively according to a variable duty cycle, wherein the variable duty cycle includes an "on" time duration and an "off" time duration, and wherein each of the plurality of scent delivery units is associated with a corresponding base scent setting; and
controlling the plurality of scent delivery units, wherein controlling the plurality of scent delivery units includes:
defining a group of scent delivery units from the plurality of scent delivery units,
receiving input indicating a scent level bias to be applied to the base scent setting of each scent delivery unit included in the group for a particular activation period, and
generating command data for each scent delivery unit included in the group, wherein the command data is generated by applying the scent level bias to the base scent setting using a predefined algorithm, wherein the predefined algorithm modifies the base scent setting using the scent level bias, and wherein when the command data is received at a scent delivery unit included in the group, the corresponding scent level or the scent delivery unit is varied based on the generated command data.

14. The method of claim 13, further comprising varying the duty cycles that are associated with each scent delivery unit included in the group of scent delivery units based on the generated command data, wherein the predefined algorithm includes an arithmetic function.

15. The method of claim 13, further comprising varying the duty cycles that are associated with each scent delivery unit included in the group of scent delivery units based on the generated command data, wherein the predefined algorithm includes a geometric function.

16. The method of claim 13, further comprising varying the duty cycles that are associated with each scent delivery unit included in the group of scent delivery units based on the generated command data, wherein each scent delivery unit in the defined group corresponds to a parameter, and wherein the parameter indicates a scent type that is associated with each scent delivery unit included in the group of scent delivery units.

17. The method of claim 13, further comprising varying cycle times that are associated with each scent delivery unit included in the group of scent delivery units based on the generated command data.

18. The method of claim 13, further comprising turning the scent delivery units on and off successively according to a variable duty cycle that ranges between 5% and 95%.

19. The method of claim 13, further comprising varying the base scent setting that is associated with each scent delivery unit included in the group of scent delivery units based on the generated command data, wherein each scent delivery unit in the defined group corresponds to a parameter, and wherein the parameter indicates a scent type that is associated with the scent delivery unit.

20. The method of claim 13, further comprising delivering scent at a variable scent level by varying one or more of fan speed, nozzle pressure, and compressor power of each scent delivery unit, and wherein, based upon a variation in the scent level bias, a central controller sends command data that indicates a corresponding variation to a corresponding one or more of fan speed, nozzle pressure, and compressor power of the scent delivery units.

21. A non-transitory computer-readable storage medium storing software comprising instructions executable by one or more computers, which, upon such execution, cause the one or more computers to perform operations comprising:
providing a plurality of scent delivery units, wherein each scent delivery unit is configured to deliver scent at a variable scent level by turning scent delivery units on and off successively according to a variable duty cycle, wherein the variable duty cycle includes an "on" time duration and an "off" time duration, and wherein each of the plurality of scent delivery units is associated with a corresponding base scent setting; and
controlling the plurality of scent delivery units, wherein controlling the plurality of scent delivery units includes:
defining a group of scent delivery units from the plurality of scent delivery units,
receiving input indicating a scent level bias to be applied to the base scent setting of each scent delivery unit included in the group for a particular activation period, and
generating command data for each scent delivery unit included in the group, wherein the command data is generated by applying the scent level bias to the base scent setting using a predefined algorithm, wherein the predefined algorithm modifies the base scent setting using the scent level bias, and wherein when the command data is received at a scent delivery unit included in the group, the corresponding scent level of the scent delivery unit is varied based on the generated command data.

22. The medium of claim 21, wherein the operations further comprise varying the duty cycles that are associated with each scent delivery unit included in the group of scent delivery units based on the generated command data, wherein the predefined algorithm includes an arithmetic function.

23. The medium of claim 21, wherein the operations further comprise varying the duty cycles that are associated with each scent delivery unit included in the group of scent delivery units based on the generated command data, wherein the predefined algorithm includes a geometric function.

24. The medium of claim 21, wherein the operations further comprise varying the duty cycles that are associated with each scent delivery unit included in the group of scent delivery units based on the generated command data, wherein each scent delivery unit in the defined group corresponds to a parameter, and wherein the parameter indicates a scent type that is associated with each scent delivery unit included in the group of scent delivery units.

25. The medium of claim 21, wherein the operations further comprise varying cycle times that are associated with each scent delivery unit included in the group of scent delivery units based on the generated command data.

26. The medium of claim 21, wherein the operations further comprise turning the scent delivery units on and off successively according to a variable duty cycle that ranges between 5% and 95%.

27. The medium of claim 21, wherein the operations further comprise varying the base scent setting that is associated with each scent delivery unit included in the group of scent delivery units based on the generated command data, wherein each scent delivery unit in the defined group corresponds to a parameter, and wherein the parameter indicates a scent type that is associated with the scent delivery unit.

28. The medium of claim 21, wherein the operations further comprise delivering scent at a variable scent level by varying one or more of fan speed, nozzle pressure, and compressor power of each scent delivery unit, and wherein, based upon a variation in the scent level bias, a central controller sends command data that indicates a corresponding variation to a corresponding one or more of fan speed, nozzle pressure, and compressor power of the scent delivery units.

* * * * *